US011732284B2

United States Patent
Kagawa et al.

(10) Patent No.: US 11,732,284 B2
(45) Date of Patent: Aug. 22, 2023

(54) TRICHODERMA REESEI MUTANT STRAIN, AND METHOD OF PRODUCING PROTEIN

(71) Applicant: Toray Industries, Inc., Tokyo (JP)

(72) Inventors: Yusuke Kagawa, Kanagawa (JP); Shingo Hiramatsu, Kanagawa (JP); Katsushige Yamada, Kanagawa (JP)

(73) Assignee: Toray Industries, Inc., Tokyo (JP)

( * ) Notice: Subject to any disclaimer, the term of this patent is extended or adjusted under 35 U.S.C. 154(b) by 84 days.

(21) Appl. No.: 17/271,958

(22) PCT Filed: Aug. 28, 2019

(86) PCT No.: PCT/JP2019/033643
§ 371 (c)(1),
(2) Date: Feb. 26, 2021

(87) PCT Pub. No.: WO2020/045473
PCT Pub. Date: Mar. 5, 2020

(65) Prior Publication Data
US 2021/0324437 A1    Oct. 21, 2021

(30) Foreign Application Priority Data
Aug. 29, 2018   (JP) .................................. 2018-160157

(51) Int. Cl.
*C12P 21/00* (2006.01)
*C12N 1/14* (2006.01)
*C12R 1/885* (2006.01)

(52) U.S. Cl.
CPC ............. *C12P 21/00* (2013.01); *C12N 1/145* (2021.05); *C12R 2001/885* (2021.05)

(58) Field of Classification Search
CPC ........... C12P 21/00; C12P 19/14; C12P 21/02; C12P 19/02; C12N 1/145; C12N 9/1048; C12N 9/2437; C12R 2001/885
See application file for complete search history.

(56) References Cited

U.S. PATENT DOCUMENTS

| 2019/0055614 A1 | 2/2019 | Kobayashi et al. |
| 2019/0169239 A1 | 6/2019 | Shibata et al. |

FOREIGN PATENT DOCUMENTS

| CN | 102311951 A | 1/2012 |
| CN | 102787108 A | 11/2012 |
| CN | 103614303 A | 3/2014 |
| JP | 2014-131501 A | 7/2014 |
| JP | 2014-150745 A | 8/2014 |
| JP | 2016-187319 A | 11/2016 |
| JP | 2018-19622 A | 2/2018 |
| WO | 2017/170918 A1 | 10/2017 |
| WO | 2018/009806 | 1/2018 |

OTHER PUBLICATIONS

National Center for Biotechnology Information, https://www.ncbi.nlm.nih.gov/protein/ETR99434.1?report=genbank&log$=protalign&blast_rank=3&RID=HPX7VCAP013, accessed Sep. 9, 2022 (Year: 2015).*
Kubicek, C. P., et al. "O-linked but not N-linked glycosylation is necessary for the secretion of endoglucanases I and II by Trichoderma reesei." Canadian journal of microbiology 33.8 (1987): 698-703. (Year: 1987).*
National Center for Biotechnology Information, O-GlcNac transferase Structures; https://www.ncbi.nlm.nih.gov/structure; accessed Dec. 14, 2022 (Year: 2022).*
Brockhausen I, Wandall HH, Hagen KGT, et al. O-GalNAc Glycans. In: Varki A, Cummings RD, Esko JD, et al., editors. Essentials of Glycobiology. 4th edition. Cold Spring Harbor (NY): Cold Spring Harbor Laboratory Press; 2022. Chapter 10. https://www.ncbi.nlm.nih.gov/books/NBK579921/ doi: 10. (Year: 2022).*
Glycosyltransferase 41; http://www.cazy.org/GT41.html; accessed Dec. 14, 2022 (Year: 2022).*
Juliano, P. et al., "Single nucleotide polymorphism analysis of a Trichoderma reesei hyper-cellulolytic mutant developed in Japan", *Bioscience, Biotechnology, and Biochemistry*, vol. 77, 2013, Issue 3, pp. 534-543.
Extended European Search Report dated Jul. 18, 2022, of counterpart European Application No. 19854337.3
Database UniProt [Online], "SubName: Full Glycosyltransferase family 41 {ECO:0000313|EMBL:EGR46476.1}; Flags: Fragment;" XP55914884, retrieved from EBI accession No. G0RR69 100% identical to SEQ ID No. 2; *abstract; sequence*, Oct. 19, 2011.
First Office Action dated Mar. 18, 2023, of counterpart Chinese Patent Application No. 201980055653.0, along with an English translation.
R. Lui et al., "Effects of VPS13 Deletion on Hyphal Branch, Sporulation and Cellulase Production in *Trichoderma reesei*," Acta Microbiologica Sinica, 57, No. 10, pp. 1555 and 1556, 2017, Abstract only in English.

* cited by examiner

*Primary Examiner* — Lora E Barnhart Driscoll
*Assistant Examiner* — Candice Lee Swift
(74) *Attorney, Agent, or Firm* — DLA Piper LLP (US)

(57) ABSTRACT

A mutant strain of *Trichoderma reesei* has a mutation that eliminates or reduces a function of a polypeptide consisting of the amino acid sequence represented by SEQ ID NO: 2. A method produces a protein, the method including a step of cultivating the mutant strain.

12 Claims, No Drawings

Specification includes a Sequence Listing.

TRICHODERMA REESEI MUTANT STRAIN, AND METHOD OF PRODUCING PROTEIN

TECHNICAL FIELD

This disclosure relates to a *Trichoderma reesei* mutant strain having an enhanced protein-producing ability and to a method of producing protein using the mutant strain.

BACKGROUND

*Trichoderma reesei* is known to have a high protein-producing ability, and studies have heretofore been made on protein production using filamentous fungi of *Trichoderma reesei*. *Trichoderma reesei* is especially excellent in terms of the ability to produce a cellulase, which is classified as a saccharifying enzyme, among proteins. For example, to further enhance cellulase production amount, overexpression or deletion of a factor that controls cellulase production is conducted.

Juliano P, Single nucleotide polymorphism analysis of a *Trichoderma reesei* hyper-cellulolytic mutant developed in Japan, Bioscience, Biotechnology, and Biochemistry, Volume 77, 2013, Issue 3, P534-543 describes that a mutant strain of *Trichoderma reesei* having a high cellulase-producing ability was acquired by reducing the function of Cre1, which is a transcription factor repressing cellulase production, among the cellulase-production-controlling factors of *Trichoderma reesei*.

As described above, a transcription factor which is one of protein-production-controlling factors in *Trichoderma reesei* has been identified, but this is considered to be merely a part of the control mechanism. It could therefore be helpful to obtain a mutant strain of *Trichoderma reesei* having a further enhanced protein-producing ability by making a search for a novel factor which controls protein production of *Trichoderma reesei*, and a method of producing protein using the mutant strain of *Trichoderma reesei*.

The Applicant hereby incorporates by reference the sequence listing contained in the ASCII text file titled NBC-21-1092 SEQ-LISTING.txt, created Feb. 25, 2021, and having 60 KB of data.

SUMMARY

We thought that if a novel control factor that had been unknown and was capable of bringing about an increase in protein production could be specified, then the amount of proteins to be produced by *Trichoderma reesei* could be further increased. We thus discovered that an improvement in protein-producing ability can be attained by cultivating a mutant strain of *Trichoderma reesei* in which a function of a polypeptide consisting of the amino acid sequence represented by SEQ ID NO: 2 has been eliminated or reduced. We thus provide (1) to (6).

(1) A mutant strain of *Trichoderma reesei*, the mutant strain having a mutation that eliminates or reduces a function of a polypeptide consisting of the amino acid sequence represented by SEQ ID NO: 2.

(2) The mutant strain according to (1), in which the mutation is a mutation that deletes a Glycosyltransferase_GTP_type domain of the polypeptide consisting of the amino acid sequence represented by SEQ ID NO: 2.

(3) The mutant strain according to (2), in which the mutation is a stop codon mutation for a glutamic acid residue at the 1,523rd residue from the N-terminal side in the amino acid sequence represented by SEQ ID NO: 2.

(4) A method of producing a protein, the method including a step of cultivating the mutant strain according to any one of (1) to (3).

(5) A method of producing a cellulase, the method including a step of cultivating the mutant strain according to any one of (1) to (3).

(6) A method of producing a sugar, the method including:
a step of producing a cellulase by the method of producing a cellulase according to (5); and
a step of saccharifying a cellulose-containing biomass by using the cellulase obtained in the step.

The mutant strain of *Trichoderma reesei* in which the function of a polypeptide consisting of the amino acid sequence represented by SEQ ID NO: 2 has been eliminated or reduced has an improved protein-producing ability and is capable of highly efficiently producing a protein compared to the parent strain into which the mutation has not been introduced. Furthermore, when the produced proteins are cellulases, an unexpected effect that the cellulases have improved various specific activities is also obtained.

DETAILED DESCRIPTION

We introduce into a parent strain of *Trichoderma reesei*, which is a microorganism originally having an excellent protein-producing ability, to thereby further enhance the protein-producing ability. Specifically, we provide a mutant strain of *Trichoderma reesei*, the mutant strain being characterized by having a mutation that eliminates or reduces the function of a polypeptide consisting of the amino acid sequence represented by SEQ ID NO: 2.

The parent strain of *Trichoderma reesei* to be used is not limited to wild strains, and mutant strains that have been improved to have an increased protein-producing ability can also be favorably used as the parent strain. For example, a mutant strain having an improved protein production property obtained by performing a mutation treatment with a mutagen, UV irradiation or the like can be utilized as the parent strain. Specific examples of mutant strains usable as the parent strain include the following known mutant strains belonging to *Trichoderma reesei*: QM6a strain (NBRC31326), QM9123 strain (ATCC24449), QM9414 strain (NBRC31329), PC-3-7 strain (ATCC66589), QM9123 strain (NBRC31327), RutC-30 strain (ATCC56765), CL-847 strain (Enzyme. Microbiol. Technol., 10, 341-346 (1988)), MCG77 strain (Biotechnol. Bioeng. Symp., 8, 89 (1978), and MCG80 strain (Biotechnol. Bioeng., 12, 451-459 (1982)). QM6a strain, QM9414 strain, and QM9123 strain are available from NBRC (NITE Biological Resource Center), and PC-3-7 strain and RutC-30 strain are available from ATCC (American Type Culture Collection).

The polypeptide consisting of the amino acid sequence represented by SEQ ID NO: 2 is a polypeptide possessed by *Trichoderma reesei* and having an overall length of 1,738 amino acid residues, and in National Center for Biotechnology Information, this polypeptide has been registered as a glycosyltransferase family 41, partial (EGR46476) that *Trichoderma reesei* QM6a strain has. Specific examples of genes encoding the polypeptide consisting of the amino acid sequence represented by SEQ ID NO: 2 include the base sequence represented by SEQ ID NO: 1.

Examples of methods of eliminating or reducing the function of the polypeptide consisting of the amino acid sequence represented by SEQ ID NO: 2 include a method of introducing a mutation that causes a total deletion of a glycosyltransferase family 41, partial or a partial deletion of a glycosyltransferase family 41, partial. Specific examples thereof include a method in which a frame shift mutation or a stop codon mutation is introduced into a gene sequence encoding the polypeptide consisting of the amino acid sequence represented by SEQ ID NO: 2, by a deletion, insertion, substitution or the like of a base.

The phrase "deletion of a glycosyltransferase family 41, partial" means a total or partial loss of the polypeptide, a change of the whole or some of the polypeptide into different amino acid(s), or a combination of these. More specifically, that phrase means that the amino acid sequence represented by SEQ ID NO: 2 comes to have a sequence identity of 80% or less with respect to the amino acid sequence of the glycosyltransferase family 41, partial. The sequence identity thereto is preferably 50% or less, more preferably 20% or less, more preferably 10% or less, more preferably 5% or less, more preferably 3% or less, more preferably 1% or less, and most preferably 0%.

CDD Search Results of National Center for Biotechnology Information disclose that the 1,338th to 1,725th amino acid residues from the N-terminal side are a Glycosyltransferase_GTP_type domain. Specific examples of when the function of a polypeptide consisting of the amino acid sequence represented by SEQ ID NO: 2 is eliminated or reduced by a mutation such as deletion, substitution, or addition, that has occurred in an amino acid sequence located in the glycosyltransferase family 41, partial include a mutation in the base sequence represented by SEQ ID NO: 1 which changes the cytosine at the 6,261st residue into adenine to thereby insert a stop codon. This mutation changes the glutamic acid residue at the 1,523rd residue in the amino acid sequence represented by SEQ ID NO: 2 into a stop codon to cause the translation to end. Since the translation thus ends in the middle of the Glycosyltransferase_GTP_type domain, which mainly performs the function of glycosyltransferase family 41, the original function of the polypeptide as a protein is eliminated.

Furthermore, the function of the polypeptide consisting of the amino acid sequence represented by SEQ ID NO: 2 may be reduced by introducing a mutation that diminishes or inhibits the expression of the polypeptide. Specifically, a mutation introduced into the promoter or terminator region of a gene encoding the amino acid sequence represented by SEQ ID NO: 2 to diminish or inhibit the expression of the polypeptide may be employed. In general, the promoter and terminator regions correspond to a region of hundreds of bases in length before and after the gene participating in transcription. Specific examples of base sequences including a promoter and a terminator that participate in transcription of the polypeptide consisting of the amino acid sequence represented by SEQ ID NO: 2 include the base sequence represented by SEQ ID NO: 1.

To introduce such mutations into the gene, use can be made of existing genetic mutation methods such as a mutation treatment with a mutagen known to those skilled in the art or with UV irradiation or the like, gene recombination such as homologous recombination using a selection marker, and a mutation by a transposon.

A mutant strain of *Trichoderma reesei* in which the function of the polypeptide consisting of the amino acid sequence represented by SEQ ID NO: 2 has been eliminated can be acquired by the following method.

The mutant strain in which all the functions of the polypeptide consisting of the amino acid sequence represented by SEQ ID NO: 2 has been eliminated or reduced can be acquired by subjecting spores of *Trichoderma reesei* as a parent strain to a genetic mutation treatment with nitrosoguanidine (NTG), ethylmethanesulfonic acid (EMS), UV or the like, and analyzing the genes of the resultant mutant strains to collect a mutant strain having the mutation by screening.

Since our mutant strain has an enhanced protein-producing ability compared to the parent strain into which the mutation has not been introduced, a culture solution of our mutant strain has a higher protein concentration than a culture solution obtained by cultivating the parent strain not having the mutation under the same cultivation conditions. When the protein is an enzyme, the enzyme has enhanced specific activity. The increasing rate in protein concentration and the increasing rate in enzyme specific activity are not particularly limited so long as the concentration and the specific activity have increased. It is, however, preferable that the increasing rates are 20% or larger.

Besides a mutation that eliminates or reduces the function of the polypeptide consisting of the amino acid sequence represented by SEQ ID NO: 2, our mutant strain may have a mutation that improves protein production amount and/or lowers the viscosity of culture solution to inhibit the degree of saturation of oxygen dissolved in the culture solution from decreasing. Specific examples thereof include a genetic mutation that reduces the function of the polypeptide represented by any of SEQ ID NOs: 3, 5, and 7.

The polypeptide consisting of the amino acid sequence represented by SEQ ID NO: 3 is a polypeptide possessed by *Trichoderma reesei* and has been registered at National Center for Biotechnology Information as predicted protein EGR50654 possessed by *Trichoderma reesei* QM6a strain. The polypeptide consisting of the amino acid sequence represented by SEQ ID NO: 3 is a polypeptide whose function is unknown, but Conserved Domain Architecture Retrieval Tool of National Center for Biotechnology Information discloses that the 95th to 277th amino acid residues from the N-terminal side have Middle domain of eukaryotic initiation factor 4G domain (hereinafter referred to as MIF4G domain) and the 380th to 485th amino acid residues from the N-terminal side have MA-3 domain. The two domains, MIF4G and MA-3, are known to have the function of binding to DNAs or RNAs (Biochem., 44, 12265-12272 (2005); Mol. Cell. Biol., 1, 147-156 (2007)). It is presumed from those disclosures that the polypeptide consisting of the amino acid sequence represented by SEQ ID NO: 3 at least has the function of binding to a DNA and/or an RNA.

Specific examples of genes encoding the polypeptide consisting of the amino acid sequence represented by SEQ ID NO: 3 include the base sequence represented by SEQ ID NO: 4. Examples of genetic mutations that reduce the function of EGR50654 include a total deletion of the MIF4G domain and/or MA-3 domain possessed by EGR50654, a partial deletion of the MIF4G domain and/or MA-3 domain, and a genetic mutation that changes the configuration relationship between the MIF4G domain and the MA-3 domain. Furthermore, the function of the polypeptide consisting of the amino acid sequence represented by SEQ ID NO: 3 can be reduced also by introducing a mutation that diminishes or inhibits the expression of the polypeptide. Specific examples of the deletion of the function of the polypeptide consisting of the amino acid sequence represented by SEQ ID NO: 3 include a mutation in the base sequence represented by SEQ ID NO: 4 which deletes any of the 1,039th to 1,044th bases.

The polypeptide consisting of the amino acid sequence represented by SEQ ID NO: 5 is a polypeptide possessed by *Trichoderma reesei* and has been registered at National Center for Biotechnology Information as predicted protein EGR44419 possessed by *Trichoderma reesei* QM6a strain.

The polypeptide consisting of the amino acid sequence represented by SEQ ID NO: 5 is a polypeptide whose function is unknown, but Conserved Domain Architecture Retrieval Tool of National Center for Biotechnology Information discloses that the 26th to 499th amino acid residues from the N-terminal side have a Sugar (and other) Transporter domain. It is presumed from that disclosure that the polypeptide consisting of the amino acid sequence represented by SEQ ID NO: 5 at least participates in transport of sugar between the inside and the outside of the fungus bodies.

Specific examples of genes encoding the polypeptide consisting of the amino acid sequence represented by SEQ ID NO: 5 include the base sequence represented by SEQ ID NO: 6. Examples of genetic mutations which reduce the function of EGR44419 include a total deletion of the Sugar (and other) Transporter domain possessed by EGR44419, a partial deletion of the Sugar (and other) Transporter domain, and a genetic mutation which changes the configuration relationship of the Sugar (and other) Transporter domain. Furthermore, the function of the polypeptide consisting of the amino acid sequence represented by SEQ ID NO: 5 can be reduced also by introducing a mutation which diminishes or inhibits the expression of the polypeptide. Specific examples of the deletion of the function of the polypeptide consisting of the amino acid sequence represented by SEQ ID NO: 5 include a mutation in the base sequence represented by SEQ ID NO: 6 which inserts 11 bases at the 1,415th position.

The polypeptide consisting of the amino acid sequence represented by SEQ ID NO: 7 is a polypeptide possessed by *Trichoderma reesei* and has been registered at National Center for Biotechnology Information as EGR48910 of a beta-adaptin large subunit possessed by *Trichoderma reesei* QM6a strain. The polypeptide consisting of the amino acid sequence represented by SEQ ID NO: 7 is one of the proteins that constitute adaptor proteins that bind to clathrin which is widely conserved in eucaryotes, and constitutes vesicles that take part in transport inside and outside the cells and inside and outside the fungus bodies (Proc. Nati. Acad. Sci. USA., 101, 14108-14113 (2004)).

Specific examples of genes encoding the polypeptide consisting of the amino acid sequence represented by SEQ ID NO: 7 include the base sequence represented by SEQ ID NO: 8. Examples of genetic mutations for EGR48910 include a mutation in the base sequence represented by SEQ ID NO: 8 that changes the cytosine at the 1,080th base into adenine.

We further provide a method of producing protein including a step of cultivating the mutant strain.

The composition of a culture medium to be used in the step of cultivating or mutant strain is not particularly limited as long as it is a culture medium composition where the *Trichoderma reesei* can produce a protein, and a known culture medium composition for microbes of the genus *Trichoderma* can be employed. As a nitrogen source, use can be made, for example, of polypeptone, bouillon, CSL, or soybean cake. An inducer for protein production may be added to the culture medium.

In producing a cellulase by our methods, the mutant strain can be cultivated in a culture medium containing one or more inducers selected from the group consisting of lactose, cellulose, and xylan. Cellulose or xylan may be added by adding a biomass containing cellulose or xylan as an inducer. Specific examples of the biomass containing cellulose or xylan include not only plants such as seed plant, pteridophyte, bryophyte, algae, and water plant, but also waste building materials. The seed plants are classified into gymnosperms and angiosperms, and both can be favorably used. The angiosperms are further classified into monocotyledons and dicotyledons. Specific examples of the monocotyledons include bagasse, switchgrass, napier grass, erianthus, corn stover, corncob, rice straw, and wheat straw, and preferred specific examples of the dicotyledons include beet pulp, eucalyptus, oak, and white birch.

The biomass containing cellulose or xylan may be a pretreated one. Methods for the pretreatment are not particularly limited, but, for example, known methods such as acid treatment, sulfuric acid treatment, dilute sulfuric acid treatment, alkali treatment, hydrothermal treatment, subcritical treatment, fine grinding treatment, and steaming treatment can be used. Pulp may be used as the biomass containing cellulose or xylan that has been subjected to such a pretreatment.

Methods for the cultivation are not particularly limited. For example, the mutant strain can be cultivated by liquid culture in which a centrifuge tube, flask, jar fermenter, tank, or the like is used or solid culture in which a plate or the like is used. It is preferred to cultivate *Trichoderma reesei* under aerobic conditions, and especially preferred among those cultivation methods is submerged culture of performing cultivation in a jar fermenter or a tank while conducting aeration or stirring. The air flow rate is preferably about 0.1-2.0 vvm, more preferably 0.3-1.5 vvm, especially preferably 0.5-1.0 vvm. The cultivation temperature is preferably about 25-35° C., more preferably 25-31° C. The pH condition during the cultivation is preferably pH 3.0-7.0, more preferably pH 4.0-6.0. As for cultivation time, the cultivation is conducted under conditions capable of protein production, until the protein is accumulated in a recoverable amount. The cultivation period is usually 24-288 hours, preferably 24-240 hours, more preferably 36-240 hours, still more preferably 36-192 hours.

Although the protein to be produced is not particularly limited, proteins excreted from the fungus bodies can be efficiently produced. Preferred of these are enzymes. More preferred are saccharifying enzymes such as cellulases, amylases, invertases, chitinases, and pectinases. Still more preferred are cellulases.

Cellulases that can be produced include various hydrolases, which include enzymes having a decomposition activity against xylan, cellulose, and hemicellulose. Specific examples thereof include cellobiohydrolase (EC 3.2.1.91) which produces cellobiose by hydrolyzing cellulose chains, endoglucanase (EC 3.2.1.4) which hydrolyzes cellulose chains from central portions thereof, β-glucosidase (EC 3.2.1.21) which hydrolyzes cellooligosaccharide and cellobiose, xylanase (EC 3.2.1.8) which is characterized by acting on hemicellulose and, in particular, on xylan, and β-xylosidase (EC 3.2.1.37) which hydrolyzes xylooligosaccharide.

Improvement in protein-producing ability or improvement in cellulase specific activity of the *Trichoderma reesei* mutant strain compared to the parent strain is ascertained by comparing culture solutions obtained by cultivating the mutant strain and the parent strain under the same conditions in protein concentration or in one or more specific activities selected from the group consisting of β-glucosidase specific activity, β-xylosidase specific activity, and cellobiohydrolase specific activity, the protein concentration and the specific activities being determined by the following methods.

The protein concentration is determined in the following manner. Culture solutions of the mutant strain and parent strain are each centrifuged at 15,000×g for 10 minutes to obtain a supernatant. The obtained supernatant is diluted, and 5 μL of the diluted supernatant is added to 250 μL of Quick Start Bradford protein assay (manufactured by Bio-Rad Laboratories, Inc.). The mixture is allowed to stand still at room temperature for 15 minutes and then examined for absorbance at 595 nm. The concentration of the protein contained in the saccharifying-enzyme solution is calculated on the basis of a calibration curve obtained using bovine serum albumin solutions as reference solutions.

The β-glucosidase specific activity is determined by the following method. First, for the supernatant of the culture solution, 10 μL of the enzyme dilution is added to 90 μL of 50 mM acetate buffer containing 1 mM p-nitrophenyl-β-glucopyranoside (produced by Sigma-Aldrich Japan), and the mixture is allowed to react at 30° C. for 10 minutes. Then, 10 μL of 2 M sodium carbonate is added and mixed well to stop the reaction, and the increase in absorbance at 405 nm is measured. Finally, release of 1 μmol of p-nitrophenol per minute is defined as 1 U of activity to calculate the specific activity.

The β-xylosidase specific activity is determined by the following method. First, for the supernatant of the culture solution, 10 μL of the enzyme dilution is added to 90 μL of 50 mM acetate buffer containing 1 mM p-nitrophenyl-β-xylopyranoside (produced by Sigma-Aldrich Japan), and the mixture is allowed to react at 30° C. for 30 minutes. Then, 10 μL of 2 M sodium carbonate is added and mixed well to stop the reaction, and the increase in absorbance at 405 nm is measured. Finally, release of 1 μmol of p-nitrophenol per minute is defined as 1 U of activity to calculate the specific activity.

The cellobiohydrolase specific activity is determined by the following method. First, for the supernatant of the culture solution, 10 μL of the enzyme dilution is added to 90 μL of 50 mM acetate buffer containing 1 mM p-nitrophenyl-β-lactopyranoside (produced by Sigma-Aldrich Japan), and the mixture is allowed to react at 30° C. for 60 minutes. Then, 10 μL of 2 M sodium carbonate is added and mixed well to stop the reaction, and the increase in absorbance at 405 nm is measured. Finally, release of 1 μmol of p-nitrophenol per minute is defined as 1 U of activity to calculate the specific activity.

Methods of recovering a protein contained in the culture solution where the mutant strain has been cultivated are not particularly limited, but the protein can be recovered by removing the fungus bodies of the mutant strain from the culture solution. Examples of methods of removing the fungus bodies include centrifugation, membrane separation, and filter press.

Furthermore, when the culture solution in which the mutant strain has been cultivated is used as a protein solution without removing the fungus bodies therefrom, the culture solution is preferably treated so that the mutant strain of *Trichoderma reesei* cannot grow therein. Examples of treatment methods for preventing the fungus bodies from growing includes heat treatment, chemical treatment, acid/alkali treatment, and UV treatment.

When the protein is an enzyme, the culture solution from which the fungus bodies have been removed or which has been treated so that the fungus bodies cannot grow, as stated above, can be used directly as an enzyme solution.

When the protein as a target to be produced is a cellulase, this cellulase can be used to saccharify cellulose-containing biomass to produce a sugar. The cellulase obtained by cultivating the mutant strain is high especially in β-glucosidase specific activity as compared with the cellulase obtained by cultivating the parent strain into which the mutation has not been introduced, and can hence efficiently decompose the cellulose-containing biomass to obtain a sugar solution having a high glucose concentration. Thus, a larger quantity of sugar can be obtained.

As for the cellulose-containing biomass to be used, the same biomass as the cellulose-containing biomass mentioned above as an inducer or the pretreated biomass can be used.

Conditions for the saccharification reaction are not particularly limited. The saccharification reaction temperature is preferably 25-60° C., especially more preferably 30° C. to 55° C. The saccharification reaction time is preferably 2 hours to 200 hours. The pH in the saccharification reaction is preferably 3.0-7.0, more preferably 4.0-6.0. In cellulases derived from the genus *Trichoderma*, the optimal pH for the reaction is 5.0. Furthermore, since the pH changes during the hydrolysis, it is preferred to add a buffer to the reaction solution or to conduct the reaction while keeping the pH constant by using an acid or an alkali.

When the enzyme is separated and recovered from the saccharified solution, use can be made of a method in which the saccharified solution is filtered with an ultrafiltration membrane or the like to recover the enzyme on the non-permeation side. According to need, a step for removing solid matter from the saccharified solution may be conducted before the filtration. The recovered enzyme can again be used for a saccharification reaction.

EXAMPLES

Our mutant strains and methods are described specifically below by referring to Examples.

Reference Example 1 Conditions for Protein Concentration Measurement

Protein concentration measuring reagent used: Quick Start Bradford protein assay (produced by Bio-Rad Laboratories, Inc.)
Measuring Conditions
  Measuring temperature: room temperature
  Protein concentration measuring reagent: 250 μL
  Culture solution of filamentous fungus: 5 μL
  Reaction time: 5 min
  Absorbance: 595 nm
  Standard: BSA Reference Example 2 Conditions for Determination of Specific Activity of Cellulases Conditions for Determination of β-Glucosidase Specific Activity
  Substrate: p-nitrophenyl-β-glucopyranoside (produced by Sigma-Aldrich Japan)
  Reaction solution: 90 μL of 50 mM acetate buffer containing 1 mM p-nitrophenyl-β-glucopyranoside
  Enzyme dilution: 10 μL
  Reaction temperature: 30° C.
  Reaction time: 10 min
  Reaction terminator: 10 μL of 2 M sodium carbonate
  Absorbance: 405 nm
Conditions for Determination of β-Xylosidase Specific Activity
  Substrate: p-nitrophenyl-β-xylopyranoside (produced by Sigma-Aldrich Japan)

Reaction solution: 90 µL of 50 mM acetate buffer containing 1 mM p-nitrophenyl-β-xylopyranoside
Enzyme dilution: 10 µL
Reaction temperature: 30° C.
Reaction time: 10 min
Reaction terminator: 10 µL of 2 M sodium carbonate
Absorbance: 405 nm
Conditions for Determination of Cellobiohydrolase Specific Activity
Substrate: p-nitrophenyl-β-lactopyranoside (produced by Sigma-Aldrich Japan)
Reaction solution: 90 µL of 50 mM acetate buffer containing 1 mM p-nitrophenyl-β-lactopyranoside
Enzyme dilution: 10 µL
Reaction temperature: 30° C.
Reaction time: 10 min
Reaction terminator: 10 µL of 2 M sodium carbonate
Absorbance: 405 nm Reference Example 3 Saccharification Test of Cellulose-Containing Biomass As cellulose-containing biomass, use was made of Arbocel (registered trademark) B800 (produced by J. Rettenmaier & Sohne) or bagasse powdered to an average particle diameter of 100 As an enzyme solution, use was made of a filtrate obtained by collecting 1 mL portion of a culture solution of either *Trichoderma reesei* or a *Trichoderma reesei* mutant strain, centrifuging the collected culture solution, recovering a supernatant from which the fungus bodies had been removed, and filtering the supernatant with 0.22 µm filter.

Saccharification Reaction

100 µL of a 1 M sodium acetate buffer was used as a buffer for saccharification reaction; 2 µL of 50 g/L erythromycin solution was used to prevent the propagation of various germs; and 0.1 g of Arbocel (registered trademark) B800 (produced by J. Rettenmaier & Sohne) or bagasse powdered to an average particle diameter of 100 µm was used as a material to be saccharified. As for enzyme solutions, an enzyme solution obtained by flask cultivation using Arbocel (registered trademark) B800 was used in an amount of 450 µL in the case of saccharifying Arbocel (registered trademark) B800 or in an amount of 400 µL in the case of saccharifying powdered bagasse. An enzyme solution obtained by flask cultivation using lactose was introduced into a measuring cylinder in an amount of 350 µL in the case of saccharifying Arbocel (registered trademark) B800 or in an amount of 400 µL in the case of saccharifying powdered bagasse, and the enzyme solution the measuring cylinder was diluted with sterilized water to 1 mL in total. The dilution was then introduced into a 2 mL tube. A saccharification reaction was conducted under temperature conditions of 50° C. for 24 hours, and then the saccharification mixture was centrifuged. The resultant supernatant was recovered as a saccharified solution, and the enzymatic reaction terminated by adding 1 N NaOH solution in an amount of one-tenth the amount of the recovered saccharified solution. The glucose concentration in the saccharified solution after termination of the reaction was determined by the UPLC shown below.

Determination of Glucose Concentration

Glucose was quantitatively analyzed under the following conditions using ACQUITY UPLC System (Waters). The quantitative analysis was performed on the basis of a calibration curve drawn with standard solutions of glucose.

Column: ACQUITY UPLC BEH Amide 1.7 µm 2.1×100 mm Column
Separation method: HILIC
Mobile phase: mobile phase A: 80% acetonitrile, 0.2% aqueous TEA solution, and mobile phase B: 30% acetonitrile, 0.2% aqueous TEA solution, in accordance with the following gradient. The gradient was a linear gradient reaching the mixing ratio corresponding to the time below.
Initiation condition: (A 99.90%, B 0.10%), 2 minutes after initiation: (A 96.70%, B 3.30%), 3.5 minutes after initiation: (A 95.00%, B 5.00%), 3.55 minutes after initiation: (A 99.90%, B 0.10%), 6 minutes after initiation: (A 99.90%, B 0.10%)
Detection method: ELSD (evaporative light scattering detector)
Flow rate: 0.3 mL/min
Temperature: 55° C.

Example 1

Preparation of *Trichoderma reesei* mutant strain in which the function of polypeptide consisting of the amino acid sequence represented by SEQ ID NO: 2 has been eliminated Method of Preparing Mutant Strain A *Trichoderma reesei* mutant strain in which the function of the polypeptide consisting of the amino acid sequence represented by SEQ ID NO: 2 has been eliminated was prepared in the following manner. A gene represented by SEQ ID NO: 1 that encodes the polypeptide consisting of the amino acid sequence represented by SEQ ID NO: 2 is destroyed by replacing the gene with acetamide as a selection marker and with acetamidase (AmdS) gene (amdS) capable of decomposing acetamide as a selection marker gene. A DNA fragment consisting of the gene sequence represented by SEQ ID NO: 9 is prepared to eliminate the function of the polypeptide consisting of the amino acid sequence represented by SEQ ID NO: 2, and *Trichoderma reesei* QM9414 strain is transformed with the DNA fragment, thereby preparing the *Trichoderma reesei* mutant strain in which the function of the polypeptide consisting of the amino acid sequence represented by SEQ ID NO: 2 has been eliminated. By this method, a *Trichoderma reesei* mutant strain is obtained in which the base sequence represented by SEQ ID NO: 1 has been deleted. To allow a DNA fragment consisting of the base sequence represented by SEQ ID NO: 1 to be introduced upstream and downstream an amdS-containing DNA sequence, a plasmid for mutation introduction is prepared to add a portion homologous to the gene sequence of the *Trichoderma reesei* QM9414 strain.

Specifically, PCR is conducted using genomic DNA extracted in a usual manner from the *Trichoderma reesei* QM9414 strain and oligo DNAs represented by SEQ ID NOs: 10 and 11, and the resulting amplified fragment is treated with restriction enzymes AflII and NotI to obtain a DNA fragment for use as the upstream DNA fragment. In addition, PCR is conducted using oligo DNAs represented by SEQ ID NOs: 12 and 13, and the resulting amplified fragment is treated with restriction enzymes MluI and SphI to obtain a DNA fragment for use as the downstream DNA fragment. The upstream and downstream DNA fragments are introduced into a plasmid to which amdS has been inserted by using restriction enzymes AflII and NotI and restriction enzymes MluI and SphI, respectively, to construct a plasmid for mutation introduction. The plasmid for mutation introduction is treated with restriction enzymes AflII and SphI, and the *Trichoderma reesei* QM9414 strain is transformed with the obtained DNA fragment which is shown by SEQ ID NO: 9. The manipulations involving the molecular biological technique are performed as described in Molecular cloning, laboratory manual, 1st, 2nd, 3rd (1989). In addition, the transformation is carried out using a standard technique, i.e., a protoplast PEG method, and specifically, is performed as described in Gene, 61, 165-176 (1987).

Preparation and Evaluation of the Mutant Strain

The *Trichoderma reesei* mutant strain acquired by the method described above was used as *Trichoderma reesei* mutant strain I in the following protein production test and experiments to determine protein concentration and cellulase specific activity.

Example 2

Protein Production Test Using *Trichoderma reesei* Mutant Strain (Preculture)

After spores of the *Trichoderma reesei* mutant strain prepared in Example 1 are diluted with physiological saline to be $1.0 \times 10^7$/mL, 2.5 mL of the diluted spore solution is inoculated into 250 mL of the preculture medium shown in Table 1 which has been placed in a 1 L baffled flask, and then is incubated on a shaker under the conditions of 28° C. and 120 rpm for 72 hours. *Trichoderma reesei* QM9414 strain is used as a control to conduct the same experiments shown below.

TABLE 1

| | |
|---|---|
| Glucose | 20 g |
| 5 × Mandel's solution* | 200 mL |
| 10 × Ammonium tartrate solution** | 100 mL |
| Corn steep liquor | 50 g |
| Trace element solution*** | 1 mL |
| Tween 80 | 0.5 mL |
| PE-M | 1 mL |
| | (per 1 L) |

*The 5 × Mandel's solution has the following composition.
7 g/L $(NH_4)_2SO_4$
10 g/L $KH_2PO_4$
2 g/L $CaCl_2 \cdot 2H_2O$
1.5 g/L $MgSO_4 \cdot 7H_2O$
**The 10 × Ammonium tartrate solution contains 92 g/L ammonium tartrate.
***The trace element solution has the following composition.
0.3 g/L $H_3BO_3$
1.3 g/L $(NH_4)_6Mo_7O_{24} \cdot 4H_2O$
5 g/L $FeCl_3 \cdot 6H_2O$
2 g/L $CuSO_4 \cdot 5H_2O$
0.4 g/L $MnCl_2 \cdot 4H_2O$
10 g/L $ZnCl_2$ Main Culture Arbocel B800 (produced by J. Rettenmaier & Sohne) is added to the main-culture medium shown in Table 2, and an investigation of submerged culture is conducted using a 5 L jar fermenter (produced by ABLE & Biott Co., Ltd.).

The preculture solutions of the *Trichoderma reesei* QM9414 strain and the *Trichoderma reesei* mutant strain prepared in Example 1 are each inoculated in an amount of 200 mL into 2.5 L of the main-culture medium to which Arbocel B800 has been added.

After the inoculation of each preculture medium into the main-culture medium, submerged culture is performed under the cultivation conditions of 28° C., 700 rpm, and an air flow rate of 100 mL/min while regulating the pH to 5.0.

TABLE 2

| | |
|---|---|
| Arbocel B800 (produced by J. Rettenmaier & Sohne) | 100 g |
| 5 × Mandel's solution* | 200 mL |
| Corn steep liquor | 25 g |
| Trace element solution*** | 1 mL |
| Tween 80 | 0.5 mL |
| PE-M | 1 mL |
| | (per 1 L) |

*Same as in Table 1.
***Same as in Table 1.

Collection of Culture Solutions

At 120 hours after initiation of the cultivation, a 20 mL portion of each of the culture solutions is collected. A part of the collected culture solution is centrifuged under the conditions of 15,000×g and 4° C. for 10 minutes to obtain a supernatant. The supernatant is filtered with a 0.22 μm filter, and the filtrate is used as a cellulase solution in the following experiments.

Determination of Protein Concentration

The protein concentration of each of the culture solutions that have been collected at 120 hours after initiation of the cultivation is determined under the conditions shown in Reference Example 1. As a result, the culture solution obtained by cultivating the *Trichoderma reesei* mutant strain in which the function of the polypeptide consisting of the amino acid sequence represented by SEQ ID NO: 2 has been eliminated has a higher protein concentration than the culture solution obtained by cultivating the *Trichoderma reesei* QM9414 strain.

Determination of Enzyme Activities

The culture solutions collected at 120 hours after initiation of the cultivation are examined for cellulase specific activities, i.e., the specific activities of β-glycosidase, β-xylosidase, and cellobiohydrolase, under the conditions shown in Reference Example 2. In determining the specific activity, an increase in absorbance at 405 nm is measured, and release of 1 μmol of the substrate per minute is defined as 1 U of activity to calculate the specific activity. As a result, the culture solution obtained by cultivating the *Trichoderma reesei* mutant strain in which the function of the polypeptide consisting of the amino acid sequence represented by SEQ ID NO: 2 has been eliminated is higher in the three specific activities than the culture solution obtained by cultivating the *Trichoderma reesei* QM9414 strain.

Flask Cultivation

Spores of the *Trichoderma reesei* mutant strain I prepared in Example 1 were diluted with physiological saline to be $1.0 \times 10^7$/mL, and 0.1 mL of the resultant spore dilution was inoculated into 10 mL of the flask culture medium containing Arbocel (registered trademark) B800 (produced by J. Rettenmaier & Sohne) or lactose shown in Table 3, that had been placed in a 50 mL baffled flask. This spore dilution was incubated on a shaker under the conditions of 28° C. and 120 rpm for 120 hours.

Furthermore, the *Trichoderma reesei* QM9414 strain, which was the parent strain into which the mutation of mutant strain I had not been introduced, was also subjected to 120 hours incubation by the method shown above, as a control for the mutant strain.

TABLE 3

| | |
|---|---|
| Arbocel B800 (produced by J. Rettenmaier & Sohne) | 20 g |
| or | |
| Lactose (produced by Kanto Chemical Co., Inc.) | 20 g |
| 5 × Mandel's solution* | 200 mL |
| 10 × Ammonium tartrate solution** | 100 mL |

TABLE 3-continued

| | |
|---|---|
| Corn steep liquor | 50 g |
| Trace element solution*** | 1 mL |
| Tween 80 | 0.5 mL |
| PE-M | 1 mL |
| | (per 1 L) |

*Same as in Table 1.
**Same as in Table 1.
***Same as in Table 1.

Collection of Culture Solutions

At 120 hours after initiation of the cultivation, 1 mL portion of each culture solution was collected. The culture solution was centrifuged under the conditions of 15,000×g and 4° C. for 10 minutes to obtain a supernatant. The supernatant was filtered with a 0.22 μm filter, and the filtrate used in the following experiments.

Determination of Protein Concentration

In the cultivation using Arbocel (registered trademark) B800, when the protein concentration in the culture solution obtained by cultivating the *Trichoderma reesei* QM9414 strain was taken as 1, then the relative value of the protein concentration in the culture solution of *Trichoderma reesei* mutant strain I was 1.2. It was thus ascertained that the mutant strain had a higher protein-producing ability than the parent strain.

Also in the cultivation using lactose, when the protein concentration in the culture solution obtained by cultivating the *Trichoderma reesei* QM9414 strain was taken as 1, then the relative value of the protein concentration in the culture solution of *Trichoderma reesei* mutant strain I was 1.3. It was thus ascertained that the mutant strain had a higher protein-producing ability than the parent strain.

Determination of Various Cellulase Specific Activities

In the cultivation using Arbocel (registered trademark) B800, when various cellulase specific activities of the culture solution obtained by cultivating the *Trichoderma reesei* QM9414 strain were taken as 1, then the relative values of the various cellulase specific activities of the culture solution obtained by cultivating the *Trichoderma reesei* mutant strain I were: a β-glucosidase specific activity of 1.1, a β-xylosidase specific activity of 1.5, and a cellobiohydrolase specific activity of 1.8. It was thus ascertained that the mutant strain had the unexpected effect of bringing about improvements also in various cellulase specific activities.

Also, in the cultivation using lactose, when various cellulase specific activities of the culture solution obtained by cultivating the *Trichoderma reesei* QM9414 strain were taken as 1, then the relative values of the various cellulase specific activities of the culture solution obtained by cultivating the *Trichoderma reesei* mutant strain I were: a β-glucosidase specific activity of 1.8, a β-xylosidase specific activity of 1.4, and a cellobiohydrolase specific activity of 1.6. It was thus ascertained that the mutant strain had the unexpected effect of bringing about improvements also in various cellulase specific activities.

Saccharification Reaction Test

In accordance with the technique described in Reference Example 3, a culture solution collected at 120 hours after initiation of the flask cultivation of *Trichoderma reesei* mutant strain I was used as cellulases to conduct a saccharification reaction test of cellulose-containing biomass. As the cellulose-containing biomass, Arbocel (registered trademark) B800 or powdered bagasse was used.

As a result, in the saccharification reaction for saccharifying Arbocel (registered trademark) B800, when the glucose concentration in the saccharified solution obtained using the cellulases obtained with the *Trichoderma reesei* QM9414 strain by the flask cultivation using Arbocel (registered trademark) B800 was taken as 1, then the relative value of the glucose concentration in the saccharified solution obtained using the cellulases obtained with *Trichoderma reesei* mutant strain I was 1.7. The relative value of the glucose concentration in the saccharified solution obtained using the cellulases obtained by the flask cultivation of the mutant strain using lactose was also 1.7.

In the saccharification reaction of saccharifying powdered bagasse, when the glucose concentration in the saccharified solution obtained using the cellulases obtained with the *Trichoderma reesei* QM9414 strain by the flask cultivation using Arbocel (registered trademark) B800 was taken as 1, then the relative value of the glucose concentration in the saccharified solution obtained using the cellulases obtained with *Trichoderma reesei* mutant strain I was 1.5. The relative value of the glucose concentration in the saccharified solution obtained using the cellulases obtained by the flask cultivation of the mutant strain using lactose was also 1.5.

It was ascertained from those results that the cellulases produced by the *Trichoderma reesei* mutant strain I were superior in enzymatic activity to the cellulases produced by the parent strain and hence had an excellent ability to produce glucose from cellulose-containing biomass.

Example 3

Preparation of *Trichoderma reesei* mutant strain in which the function of polypeptide consisting of amino acid sequence represented by SEQ ID NO: 2 has been eliminated (2)

A QM9414-A strain, which was a strain obtained by passage culture of *Trichoderma reesei* QM9414 strain, was subjected to a genetic mutation treatment to acquire a QM9414-C strain as a mutant strain. The genetic mutation treatment was conducted in the following manner. Spores of the QM9414-A strain were inoculated into the preculture medium shown in Table 1 so that $1.0 \times 10^5$ spores were inoculated per mL of the preculture medium. 15 mL of the preculture medium was incubated for a half day and then centrifuged to recover the spores. The recovered spores were suspended in a Tris-maleate buffer (pH 6.0) to give a 10-mL spore solution, and 0.5 mL of an NTG solution obtained by dissolution with a Tris-maleate buffer (pH 6.0) so as to result in a concentration of 1.0 g/L was added thereto. The resultant mixture was held at 28° C. for 100 minutes to perform the genetic mutation treatment. The spores that had undergone the genetic mutation treatment were recovered by centrifuging, subsequently rinsed with a Tris-maleate buffer (pH 6.0) three times, and finally suspended as genetic-mutation-treated spores in 10 mL of a Tris-maleate buffer (pH 6.0). The genetic-mutation-treated spores were added to an agar medium prepared by adding crystalline cellulose. The size of halos that surrounded colonies and indicated regions where the crystalline cellulose had been decomposed by cellulases, was used as an index to select a QM9414-C strain that had formed a large halo.

The QM9414-C strain was genetically analyzed and, as a result, we found that the cytosine at the 6,261st residue in the base sequence represented by SEQ ID NO: 1 had been changed to adenine. This mutation changes the glutamic acid residue at the 1,523rd residue in the amino acid sequence represented by SEQ ID NO: 2 into a stop codon and causes a deletion of a Glycosyltransferase_GTP_type domain of the polypeptide consisting of the amino acid sequence represented by SEQ ID NO: 2.

Example 4

Protein Production Test Using *Trichoderma reesei* Mutant Strain in which the function of polypeptide consisting of amino acid sequence represented by SEQ ID NO: 2 has been eliminated Determination of Protein Concentration and Various Cellulase Specific Activities The QM9414-C strain acquired in Example 3, which was a *Trichoderma reesei* mutant strain in which the function of the polypeptide consisting of the amino acid sequence represented by SEQ ID NO: 2 had been eliminated, was cultivated in the same manner as in Example 2, and the culture solution collected at 120 hours after initiation of the cultivation was examined for protein concentration and cellulase specific activities under the conditions shown in Reference Examples 1 and 2. As for a control, the QM9414-A strain which was the parent strain of the QM9414-C strain was used.

The results thereof are as shown in Table 4. The culture solution of the QM9414-C strain had a relative value of protein concentration being 2.6 times that of the culture solution of QM9414-A strain. Furthermore, the various specific activities of the culture solution of the QM9414-C strain, in terms of relative value with respect to those for the QM9414-A strain, were: 3.1 times for β-glucosidase, 1.5 times for β-xylosidase, and 2.0 times for cellobiohydrolase.

TABLE 4

| | QM9414-A Strain | QM9414-C Strain |
|---|---|---|
| Relative value of protein concentration | 1.0 | 2.6 |
| Relative value of β-glucosidase specific activity | 1.0 | 3.1 |
| Relative value of β-xylosidase specific activity | 1.0 | 1.5 |
| Relative value of cellobiohydrolase specific activity | 1.0 | 2.0 |

Saccharification Reaction Test

In accordance with the technique described in Reference Example 3, a culture solution collected at 120 hours after initiation of the cultivation of the *Trichoderma reesei* QM9414-C strain was used as cellulases to conduct a saccharification reaction test of cellulose-containing biomass. As the cellulose-containing biomass, Arbocel (registered trademark) B800 or powdered bagasse was used.

As a result, when the glucose concentration in the saccharified solution obtained using the cellulases obtained with the *Trichoderma reesei* QM9414-A strain was taken as 1, then the relative value of the glucose concentration in the saccharified solution obtained using the cellulases obtained with *Trichoderma reesei* QM9414-C strain was 1.1 in the saccharification of Arbocel (registered trademark) B800 and was 1.2 in the saccharification of powdered bagasse.

We ascertained from those results that the cellulases produced by *Trichoderma reesei* QM9414-C strain were superior in enzymatic activity to the cellulases produced by the parent strain and hence had an excellent ability to produce glucose from cellulose-containing biomass.

The invention claimed is:

1. A mutant strain of *Trichoderma reesei* wherein a parent strain encodes a polypeptide consisting of the amino acid sequence represented by SEQ ID NO: 2, and the mutant strain has a mutation that eliminates or reduces an expression of the polypeptide.

2. The mutant strain of claim 1, wherein the mutation results in the deletion of a Glycosyltransferase_GTP_type domain of SEQ ID NO: 2, the Glycosyltransferase_GTP_type domain being 1,338th to 1,725th amino acid residues from an N-terminal side.

3. The mutant strain of claim 2, wherein the mutation is a stop codon for a glutamic acid codon corresponding to the 1,523rd residue from the N-terminal side in the amino acid sequence represented by the SEQ ID NO: 2 in a gene encoding the polypeptide consisting of the amino acid sequence represented by SEQ ID NO: 2.

4. A method of producing a protein, the method comprising a step of cultivating the mutant strain according to claim 1.

5. A method of producing a protein, the method comprising a step of cultivating the mutant strain according to claim 2.

6. A method of producing a protein, the method comprising a step of cultivating the mutant strain according to claim 3.

7. A method of producing a cellulase, the method comprising a step of cultivating the mutant strain according to claim 1.

8. A method of producing a cellulase, the method comprising a step of cultivating the mutant strain according to claim 2.

9. A method of producing a cellulase, the method comprising a step of cultivating the mutant strain according to claim 3.

10. A method of producing a sugar comprising:
a step of producing a cellulase by the method of producing a cellulase according to claim 7; and
a step of saccharifying a cellulose-containing biomass by using the cellulase obtained in the step.

11. A method of producing a sugar comprising:
a step of producing a cellulase by the method of producing a cellulase according to claim 8; and
a step of saccharifying a cellulose-containing biomass by using the cellulase obtained in the step.

12. A method of producing a sugar comprising:
a step of producing a cellulase by the method of producing a cellulase according to claim 9; and
a step of saccharifying a cellulose-containing biomass by using the cellulase obtained in the step.

* * * * *

SEQUENCE LISTING

```
<160> NUMBER OF SEQ ID NOS: 13

<210> SEQ ID NO 1
<211> LENGTH: 7056
<212> TYPE: DNA
<213> ORGANISM: Trichoderma reesei

<400> SEQUENCE: 1
atgctttctc ccctgcgctc gcggcttgtg aaagccacat tcctgggcac atgtcgccaa      60
gtgcgattgg cctcttcagc gagatatccc caggccgtct cgcctctagc ctttgacctc     120
cattcgcctt cccacccgag taaagatgag aagacggctc ccatcatctt cctgcatggt     180
ctctttgggt ccaagaagaa caacagggca atcagcaagt aagcgatgat tcatcgtgtg     240
ctgtcatggt ctctagctta caatatcgta gagccctggc ccgagacttg aagactcatg     300
tatacacggt ggtaggtgaa gtctgcgagg ctgttcaagc aagtttcatc agcgactaaa     360
caggaatgaa ggatctgaga aaccacggag aatctcccca cgatccccgc cacgactatg     420
tcgccatgac cgaggacctg ttggccttca ttgaccagca tggtctcaaa gaacctactc     480
tgataggcca ttccatgtac ggctcatctg agactgcggg aagccctgac agccggctga     540
tgtatggatt gcaggggcgc caagacggcc atgtcggcag ccctgcgctc gccagagacg     600
gtggccaagg tcgttgcggt tgacaacgca cctgtcgatg tcacgctgag caggacgttt     660
gcttcctacg tccggggcat gaagaagatt gaagaggcca aagtcactcg ccagtccgag     720
gccgacgcca tcctgcgaga ctacgaagag gtcaatgccg ccgctgctcc ttgatgcgaa     780
tcatcgccga gacaagaact gacagtgtct tgcaaacagt cgctcccgat ccgccagttt     840
ctgctcggaa acctgtatcg ctcacctgaa gacggcatcc agaggtttcg cgtcccttg      900
```

```
gacatactcg gtcgatcact cgaccacctc ggagactttc cctacaagaa cccaggcgag    960
gcacgctaca caaagcccgc cctctttgtt cgaggcaccc agagcaaata cgtgccggac   1020
gacgtgctgc ccatcattgg ccagttcttc ccgcgctttc aattggtgga catcgatgcc   1080
ggccactggc taatatcgga gcagcctgag gccttcagac aaggtaattt aaatcaaatc   1140
acaaacacca acacacttgt ccggatctgc gttaatgaca cacacccaca acagccgtcg   1200
tgagcttctt gcaagatcct gaaacagcgc aatagagaga gaaaggtgag attgttagac   1260
cattatagag caccttactt tagacgatta tataatgtgt atcttgcgat ttccatcact   1320
tttgaatgct tgaccccata cctagaattc tactaccttc tacactatac caagctgtat   1380
ccaggtaggt tttcatgtac ccgtactcgt accttgctag tgttggtcct gcattcggtc   1440
acagtgtcag gctgccgttc atcctcatac cagattgcga tgttgcagca tctctcctaa   1500
ttgccaaaca ggccctttgc ccccttttgg tgagggaaac cgcatatctc gattccttgg   1560
aagcactcga gcaaacaaat gccttgtacc ccaaaggtat tccttggctg acacatcccc   1620
ccgcactgtg tacatgcagc ttgcatgccc gagtaacgca ggcgttagcc agtgccaccc   1680
actctacatc ataccccccc tgcttgattc acccagcctc gaggctccct agctcagccc   1740
gtttgtcact actactgcac gcttcccttg ccttgctcga aactccatgc tgcgtctgcg   1800
tctgcgtttg ctcgtttgca aggtagagat acagtacggc gcacaaaccc ggacccggta   1860
cctcgagaag cggcattaga ctggccgacg ggagggtaag tcagtgtcaa gtcacgtcct   1920
ctacctgtgc cgctgttgca gctgctggcc ccgtgcacat cagcgcagcg cctcagcccc   1980
cgatgcctgc cggcgtcctc agccatgatg tgaacggcat cgacattgct gctcgtccgc   2040
aagtggttct gcttctcgct ccttgactcg acctagagcc cgcgctcgcc tttgtcctcg   2100
ccatcgccat cgccctcgcc ctcgccctcc aaaccctcgc ccgccatcga acccgccgct   2160
accatccgtc gtgggcatgt tgcccctagt ccagacgcac ccgcgcgtgg tgcctgttcc   2220
cctcgacttc gagtcttttg gagcgccggc tgccaggccc gaagctgaca gacgagccgt   2280
cgcgtcgccc taccatcgcg gcgtctctca ctcatacggc ggccccgtca gcgctgctcc   2340
cgccggccaa ggctcgcgag accacgacta ccatctgcgc cgcaagacgc ctcggggcac   2400
catcgacgcc ggctacgatg ggtcgccgac gcagctgtcg cccggcccgc caccgctcaa   2460
gcagctgatc cttccgacgc cctctggcat ctatccctac gttcctccaa acaacctgcc   2520
ctttcacgcc aagcctcgtc tctcgaacac cgacccgata agcctgggac aagctcctgc   2580
ggtctcgccg tggtccctca gctatggggg gcagaacttc gttctctcca gcggatcccc   2640
catggtcccc cagccgggac catcatggca accctatgga taccccatgt tcagccaggt   2700
tccaggcatg catcagccgc ttatgagggc ggcagagtac aatgtgcgtg ccttttgtcc   2760
gcccccggcc tccgcccctg atgccgcgac attcaatcag tttggctggc agctgggcgc   2820
ttcgcagcag aatctcggct acttcgatca gtcccaatac cctgaaccga ggtctatgct   2880
gcttcctgcc agcttctcac accatacgtc agatgtccaa ctcccataca ggcccgttcc   2940
ggatttcaag gccggcctcg aagtaacttc atttcccctca caaccattgg tgcaggggag   3000
ctatctgggc cagagctcgc ttgtggagga tgttcccgcc ggcgaacaat atgccgtcca   3060
agcgagtttt acggaaaagg tctactcaaa gcccaggac cattatgttg aactgctggc   3120
ctacctgcaa acggctagga ggcttgatca gatgagtact ggcggcaatt ccagctcaag   3180
gtttaaagtt ctggtatttc caaggccccc aaagtctaga aaggagcatt ttggtacctt   3240
```

```
tcgaggttta aataaccgtt ttgagcggcc tactgtgtcg gccatcatgc caaccagcca   3300
tcctggggca ttgacatcga atatcgagga tactctgagc aacaacacag gccatcgat   3360
gggacaagat gtccatgtgg aagctcatcg gcgtcgtacc tcggcaacac attttcgtac   3420
ctcatccaac gtctacaccc catcctcgtc atttggcgca gttggtccgg ttgccatggc   3480
gaaagcgtta ccaattctga acgcaaaaag ctcgtttgac atgttgaaga atctatgtga   3540
gcagagtaac tggaagtgga ttgatggaat cttactcggt gggtgtctgt tatatggcct   3600
ctcgcggttc gaggatgccg tggagtggtt ctccagagtt cttactctag attcaaggtt   3660
tgacctgttc cagatgaact atcaagtggt tgttctctat ctgactcaga ttatagccat   3720
gtcgaggcca tcacgaattt agccgctacg ctctattgcc tgaaccgcca ggaggaagct   3780
gagcagcatt ggctgagagc cattaagctg cgccccgacc atctagaggc cacggaacag   3840
ctcgtcgggc tgctgtacaa gaaacggagc cgggaggcga tcgacatcat ttgcttcgtg   3900
caacaagcgt tgagtttgaa gagaggaagt ccaaaccgga cgagctaccc tgcctccagc   3960
gatgactgtc ttcctagcca acagccatcg aaatttgcag cgcccttttag ctatcattac   4020
gagaccgcct ctacgacgag tggccatagc tccaggcgct ctgatttcgg gtccagcgga   4080
tatgcgctcc ccaacagtga aaacggccgg attttggcac tggttcacgc caaaggcaca   4140
atactatatg gtctgaagga tatcgagagg gcttcggagg cgttcgaaga agctgtgctg   4200
ataagtgttg gggagcgcat acgaagcgtc caagacttgg ttaaccggat ccatgctgtc   4260
ctcgcgccgg cagggtcaca ctcgactggc agtgaccgta gaccggtttc tcggcggccc   4320
ctcttgctcc cccctgagaa ggctcgccaa actgcccatc ttgtatttgc tgctgatggc   4380
ggaggtagcg aactgcccgg gctggcgttc gttcccgaag gcgcagcaag gcgggtcgcc   4440
gtgcaaacga cgagcaatgc tctgctctcc ctagccaaga ttttccagga cgcaatgtct   4500
ggcgggagca ctgtgcccag tctgctgagg cagcccacgg gtattggcga catcctggcg   4560
ttgtactatc tttcgctttc cctccaagag agtccctcta cagcaaacaa tatcggcatc   4620
ctccttgcgg gcgtgcagca gacggcacca agcaatgtca cgacgccagg aacggtccct   4680
cctcggccca gtctccccgg cgtcgtacct ggcagcggcc ttgctctcgc cttggcctac   4740
tataactacg ggctgcgtct cgatccgaga catgttcacc tgcacaccaa tcttggcagc   4800
cttctcaagg acgttggcca gctggaccct gcaatccaga tgtacgagcg ggcggtgtca   4860
tgcgacagga cgtttgatat cgctctgacc aacctagcca atgcagtcaa agacaagggt   4920
cgcatcaagg atgccattgc ctattacagg cgagcggtgg actcgaaccc cgatttcgcc   4980
gaagccgtct gcgggctctt gacggccctc aactccgtat gcgattggcg tggcagaggt   5040
ggagcgctgc tggaatcggg caaatatgac cgatggcacg ttgacgatga gggtaccctg   5100
gtcgacgtgc ggacggccat gcatggcagc ggcctcaccc agcgagtgat tggcattata   5160
agtcagcagc tggacgacgc atcgcaatgg ggccgcggca tactgcaaca gccgaccatc   5220
cacgggctgg tggaacagct ccaggaattc tgccacaacc ccaagtttga cctggaaaac   5280
gccatccgtg cctgggctca taaatcgtgg gaaggctccc gcttggttcg cctcgtggaa   5340
cgggcgacaa gggtcatctt gtggaaatgg tatcatgatc ggcatgtcgc ccaaaggaag   5400
gcgacgccct cgcagtatta tcggcctcag ctgccctctt ctctcaccat accatctgcg   5460
ccaactgtgc ttcccttcca caccttcacg taccgctat ctgccaagga catacggtcc   5520
atctcccagc gcaatgcaat gcggatatcg tgctcgacgc ttcgggcccc ttggctgccg   5580
cccacggtgt atccgccacc acctccgcca aaccccttatc tgaacgttgg atacgtgtcg   5640
```

-continued

```
tcagacttca acaaccaccc gctagctcac ctgtaagaag catccctctt gcgtgtgacg    5700
ccttggctcg tgaagcacag tatgctaaca tgcttcggca ccatcacagg atgcagtcgg    5760
tatttggatt ccacaaccct caacgtgccc gggccttctg ctatgccacc actcccagtg    5820
acaagtccat acatcggcaa cagatcgaaa gagaggcgcc tgtgtttcgt gatgtcagtt    5880
cctggccggc agagaagtta attgaacaga ttgtccgcga tgagattcac atactagtta    5940
atctcaatgg ctacaccaga ggtgctcgga acgaaatatt cgctgctcgc ccggccccta    6000
tccagatgtc ctttatggga ttcgccggga cgcttggtgc ggagtggtgc gactacctcc    6060
tcgccgacac aacggccgtc ccccgagca ctttgcgccc ttggaggaac aacaccacca    6120
tagaagacgt gtttcaggac atgaccgagg gggatgagcg ccagtggatg tactcggaga    6180
acatcatatt ctgccgagac acgttcttct gctgtgatca cgcgcagtcg tgcgatgata    6240
atgaacgcga catgacgtgg gaggatgaag agaggcgtcg ctggaagatg cgcaaggaac    6300
tatttccgac aatcgcagac gatgccatca tcctggccaa cttaatcaa ctctacaagg     6360 caagtaaagc ttgcatgaaa tggccagctt gtagtactct tcccagctaa cctgatggta    6420
gattgacccg actacattcc gatcttggtt acgaatcctc gccaggactc ccaaggccat    6480
actctggctt ctacggttcc ctgaactagg agagaccaat ttgcgacaaa cggccgaggc    6540
ctgggccggg gcagaggtgg ccagtcggct cgtcttcact gacgttgcgc aaagaacca    6600 gcacatcaac agggctagag tatgcgatct gttcctcgat actgcggagt gcaacgcgca    6660
caccactgcc gccgatgtcc tgtggtcgag cactcctctc ctcaccttgc ctcggtattc    6720
gtacaagatg tgctcccgga tggcggcgtc catcctgcga ggcgcgctgc ccaagtcggc    6780
agagggtcaa caggcagcac tggaactgat cgcggatggc gagacggaat acgaggatca    6840
agccgcagaa ctagccgggg ggctcactta cgtgatgacg gatgagggat acggtcgggg    6900
caaggggcgt ctagcagagc tacgaaaact gctttgggat agcagatgga gctgcggact    6960
cttcaacaca cggcggtggg taaacgatct ggaaagggct tacgaggagg catggcgacg    7020
gtgggttgcg ggcaagggcg gtgacatata tctgtg                             7056
```

<210> SEQ ID NO 2
<211> LENGTH: 1738
<212> TYPE: PRT
<213> ORGANISM: Trichoderma reesei

<400> SEQUENCE: 2

Met Leu Ser Pro Leu Arg Ser Arg Leu Val Lys Ala Thr Phe Leu Gly
1               5                   10                  15

Thr Cys Arg Gln Val Arg Leu Ala Ser Ser Ala Arg Tyr Pro Gln Ala
            20                  25                  30

Val Ser Pro Leu Ala Phe Asp Leu His Ser Pro Ser His Pro Ser Lys
        35                  40                  45

Asp Glu Lys Thr Ala Pro Ile Ile Phe Leu His Gly Leu Phe Gly Ser
    50                  55                  60

Lys Lys Asn Asn Arg Ala Ile Ser Lys Ala Leu Ala Arg Asp Leu Lys
65                  70                  75                  80

Thr His Val Tyr Thr Val Asp Leu Arg Asn His Gly Glu Ser Pro His
                85                  90                  95

Asp Pro Arg His Asp Tyr Val Ala Met Thr Glu Asp Leu Leu Ala Phe
            100                 105                 110

Ile Asp Gln His Gly Leu Lys Glu Pro Thr Leu Ile Gly His Ser Met

-continued

```
                115                 120                 125
Gly Ala Lys Thr Ala Met Ser Ala Ala Leu Arg Ser Pro Glu Thr Val
        130                 135                 140
Ala Lys Val Val Ala Val Asp Asn Ala Pro Val Asp Val Thr Leu Ser
145                 150                 155                 160
Arg Thr Phe Ala Ser Tyr Val Arg Gly Met Lys Lys Ile Glu Glu Ala
                165                 170                 175
Lys Val Thr Arg Gln Ser Glu Ala Asp Ala Ile Leu Arg Asp Tyr Glu
            180                 185                 190
Glu Ser Leu Pro Ile Arg Gln Phe Leu Leu Gly Asn Leu Tyr Arg Ser
        195                 200                 205
Pro Glu Asp Gly Ile Gln Arg Phe Arg Val Pro Leu Asp Ile Leu Gly
    210                 215                 220
Arg Ser Leu Asp His Leu Gly Asp Phe Pro Tyr Lys Asn Pro Gly Glu
225                 230                 235                 240
Ala Arg Tyr Thr Lys Pro Ala Leu Phe Val Arg Gly Thr Gln Ser Lys
                245                 250                 255
Tyr Val Pro Asp Asp Val Leu Pro Ile Ile Gly Gln Phe Phe Pro Arg
            260                 265                 270
Phe Gln Leu Val Asp Ile Asp Ala Gly His Trp Leu Ile Ser Glu Gln
        275                 280                 285
Pro Glu Ala Phe Arg Gln Glu Phe Tyr Tyr Leu Leu His Tyr Thr Lys
    290                 295                 300
Leu Tyr Pro Gly Arg Asp Thr Val Arg Arg Thr Asn Pro Asp Pro Val
305                 310                 315                 320
Pro Arg Glu Ala Ala Leu Asp Trp Pro Thr Gly Gly Ala Arg Ala Arg
                325                 330                 335
Leu Cys Pro Arg His Arg His Arg Pro Arg Pro Arg Pro Pro Asn Pro
            340                 345                 350
Arg Pro Pro Ser Asn Pro Pro Leu Pro Ser Val Val Gly Met Leu Pro
        355                 360                 365
Leu Val Gln Thr His Pro Arg Val Val Pro Val Pro Leu Asp Phe Glu
    370                 375                 380
Ser Phe Gly Ala Pro Ala Ala Arg Pro Glu Ala Asp Arg Arg Ala Val
385                 390                 395                 400
Ala Ser Pro Tyr His Arg Gly Val Ser His Ser Tyr Gly Gly Pro Val
                405                 410                 415
Ser Ala Ala Pro Ala Gly Gln Gly Ser Arg Asp His Asp Tyr His Leu
            420                 425                 430
Arg Arg Lys Thr Pro Arg Gly Thr Ile Asp Ala Gly Tyr Asp Gly Ser
        435                 440                 445
Pro Thr Gln Leu Ser Pro Gly Pro Pro Leu Lys Gln Leu Ile Leu
    450                 455                 460
Pro Thr Pro Ser Gly Ile Tyr Pro Tyr Val Pro Pro Asn Asn Leu Pro
465                 470                 475                 480
Phe His Ala Lys Pro Arg Leu Ser Asn Thr Asp Pro Ile Ser Leu Gly
                485                 490                 495
Gln Ala Pro Ala Val Ser Pro Trp Ser Leu Ser Tyr Gly Gly Gln Asn
            500                 505                 510
Phe Val Leu Ser Ser Gly Ser Pro Met Val Pro Gln Pro Gly Pro Ser
        515                 520                 525
Trp Gln Pro Tyr Gly Tyr Pro Met Phe Ser Gln Val Pro Gly Met His
    530                 535                 540
```

```
Gln Pro Leu Met Arg Ala Ala Glu Tyr Asn Val Arg Ala Phe Cys Pro
545                 550                 555                 560

Pro Pro Ala Ser Ala Pro Asp Ala Ala Thr Phe Asn Gln Phe Gly Trp
            565                 570                 575

Gln Leu Gly Ala Ser Gln Gln Asn Leu Gly Tyr Phe Asp Gln Ser Gln
            580                 585                 590

Tyr Pro Glu Pro Arg Ser Met Leu Leu Pro Ala Ser Phe Ser His His
        595                 600                 605

Thr Ser Asp Val Gln Leu Pro Tyr Arg Pro Val Pro Asp Phe Lys Ala
        610                 615                 620

Gly Leu Glu Val Thr Ser Phe Pro Ser Gln Pro Leu Val Gln Gly Ser
625                 630                 635                 640

Tyr Leu Gly Gln Ser Ser Leu Val Glu Asp Val Pro Ala Gly Glu Gln
                645                 650                 655

Tyr Ala Val Gln Ala Ser Phe Thr Glu Lys Val Tyr Ser Lys Ala Gln
                660                 665                 670

Asp His Tyr Val Glu Leu Leu Ala Tyr Leu Gln Thr Ala Arg Arg Leu
            675                 680                 685

Asp Gln Met Ser Thr Gly Gly Asn Ser Ser Ser His Val Glu Ala
690                 695                 700

Ile Thr Asn Leu Ala Ala Thr Leu Tyr Cys Leu Asn Arg Gln Glu Glu
705                 710                 715                 720

Ala Glu Gln His Trp Leu Arg Ala Ile Lys Leu Arg Pro Asp His Leu
                725                 730                 735

Glu Ala Thr Glu Gln Leu Val Gly Leu Leu Tyr Lys Lys Arg Ser Arg
                740                 745                 750

Glu Ala Ile Asp Ile Ile Cys Phe Val Gln Gln Ala Leu Ser Leu Lys
                755                 760                 765

Arg Gly Ser Pro Asn Arg Thr Ser Tyr Pro Ala Ser Ser Asp Asp Cys
770                 775                 780

Leu Pro Ser Gln Gln Pro Ser Lys Phe Ala Ala Pro Phe Ser Tyr His
785                 790                 795                 800

Tyr Glu Thr Ala Ser Thr Thr Ser Gly His Ser Ser Arg Arg Ser Asp
                805                 810                 815

Phe Gly Ser Ser Gly Tyr Ala Leu Pro Asn Ser Glu Asn Gly Arg Ile
                820                 825                 830

Leu Ala Leu Val His Ala Lys Gly Thr Ile Leu Tyr Gly Leu Lys Asp
                835                 840                 845

Ile Glu Arg Ala Ser Glu Ala Phe Glu Glu Ala Val Leu Ile Ser Val
                850                 855                 860

Gly Glu Arg Ile Arg Ser Val Gln Asp Leu Val Asn Arg Ile His Ala
865                 870                 875                 880

Val Leu Ala Pro Ala Gly Ser His Ser Thr Gly Ser Asp Arg Arg Pro
                885                 890                 895

Val Ser Arg Arg Pro Leu Leu Leu Pro Glu Lys Ala Arg Gln Thr
                900                 905                 910

Ala His Leu Val Phe Ala Ala Asp Gly Gly Gly Ser Glu Leu Pro Gly
            915                 920                 925

Leu Ala Phe Val Pro Glu Gly Ala Ala Arg Arg Val Ala Val Gln Thr
            930                 935                 940

Thr Ser Asn Ala Leu Leu Ser Leu Ala Lys Ile Phe Gln Asp Ala Met
945                 950                 955                 960
```

Ser Gly Gly Ser Thr Val Pro Ser Leu Leu Arg Gln Pro Thr Gly Ile
965 970 975

Gly Asp Ile Leu Ala Leu Tyr Tyr Leu Ser Leu Ser Leu Gln Glu Ser
980 985 990

Pro Ser Thr Ala Asn Asn Ile Gly Ile Leu Leu Ala Gly Val Gln Gln
995 1000 1005

Thr Ala Pro Ser Asn Val Thr Thr Pro Gly Thr Val Pro Pro Arg
1010 1015 1020

Pro Ser Leu Pro Gly Val Val Pro Gly Ser Gly Leu Ala Leu Ala
1025 1030 1035

Leu Ala Tyr Tyr Asn Tyr Gly Leu Arg Leu Asp Pro Arg His Val
1040 1045 1050

His Leu His Thr Asn Leu Gly Ser Leu Leu Lys Asp Val Gly Gln
1055 1060 1065

Leu Asp Leu Ala Ile Gln Met Tyr Glu Arg Ala Val Ser Cys Asp
1070 1075 1080

Arg Thr Phe Asp Ile Ala Leu Thr Asn Leu Ala Asn Ala Val Lys
1085 1090 1095

Asp Lys Gly Arg Ile Lys Asp Ala Ile Ala Tyr Tyr Arg Arg Ala
1100 1105 1110

Val Asp Ser Asn Pro Asp Phe Ala Glu Ala Val Cys Gly Leu Leu
1115 1120 1125

Thr Ala Leu Asn Ser Val Cys Asp Trp Arg Gly Arg Gly Gly Ala
1130 1135 1140

Leu Leu Glu Ser Gly Lys Tyr Asp Arg Trp His Val Asp Asp Glu
1145 1150 1155

Gly Thr Leu Val Asp Val Arg Thr Ala Met His Gly Ser Gly Leu
1160 1165 1170

Thr Gln Arg Val Ile Gly Ile Ile Ser Gln Gln Leu Asp Asp Ala
1175 1180 1185

Ser Gln Trp Gly Arg Gly Ile Leu Gln Gln Pro Thr Ile His Gly
1190 1195 1200

Leu Val Glu Gln Leu Gln Glu Phe Cys His Asn Pro Lys Phe Asp
1205 1210 1215

Leu Glu Asn Ala Ile Arg Ala Trp Ala His Lys Ser Trp Glu Gly
1220 1225 1230

Ser Arg Leu Val Arg Leu Val Glu Arg Ala Thr Arg Val Ile Leu
1235 1240 1245

Trp Lys Trp Tyr His Asp Arg His Val Ala Gln Arg Lys Ala Thr
1250 1255 1260

Pro Ser Gln Tyr Tyr Arg Pro Gln Leu Pro Ser Ser Leu Thr Ile
1265 1270 1275

Pro Ser Ala Pro Thr Val Leu Pro Phe His Thr Phe Thr Tyr Pro
1280 1285 1290

Leu Ser Ala Lys Asp Ile Arg Ser Ile Ser Gln Arg Asn Ala Met
1295 1300 1305

Arg Ile Ser Cys Ser Thr Leu Arg Ala Pro Trp Leu Pro Pro Thr
1310 1315 1320

Val Tyr Pro Pro Pro Pro Pro Asn Pro Tyr Leu Asn Val Gly
1325 1330 1335

Tyr Val Ser Ser Asp Phe Asn Asn His Pro Leu Ala His Leu Met
1340 1345 1350

Gln Ser Val Phe Gly Phe His Asn Pro Gln Arg Ala Arg Ala Phe

|     |     |     |     |     |     |     |     |     |     |     |     |
| --- | --- | --- | --- | --- | --- | --- | --- | --- | --- | --- | --- |
|     | 1355 |     |     |     | 1360 |     |     |     | 1365 |     |     |
| Cys | Tyr | Ala | Thr | Thr | Pro | Ser | Asp | Lys | Ser | Ile | His | Arg | Gln | Gln |
|     | 1370 |     |     |     | 1375 |     |     |     | 1380 |     |     |
| Ile | Glu | Arg | Glu | Ala | Pro | Val | Phe | Arg | Asp | Val | Ser | Ser | Trp | Pro |
|     | 1385 |     |     |     | 1390 |     |     |     | 1395 |     |     |
| Ala | Glu | Lys | Leu | Ile | Glu | Gln | Ile | Val | Arg | Asp | Glu | Ile | His | Ile |
|     | 1400 |     |     |     | 1405 |     |     |     | 1410 |     |     |
| Leu | Val | Asn | Leu | Asn | Gly | Tyr | Thr | Arg | Gly | Ala | Arg | Asn | Glu | Ile |
|     | 1415 |     |     |     | 1420 |     |     |     | 1425 |     |     |
| Phe | Ala | Ala | Arg | Pro | Ala | Pro | Ile | Gln | Met | Ser | Phe | Met | Gly | Phe |
|     | 1430 |     |     |     | 1435 |     |     |     | 1440 |     |     |
| Ala | Gly | Thr | Leu | Gly | Ala | Glu | Trp | Cys | Asp | Tyr | Leu | Leu | Ala | Asp |
|     | 1445 |     |     |     | 1450 |     |     |     | 1455 |     |     |
| Thr | Thr | Ala | Val | Pro | Pro | Ser | Thr | Leu | Arg | Pro | Trp | Arg | Asn | Asn |
|     | 1460 |     |     |     | 1465 |     |     |     | 1470 |     |     |
| Thr | Thr | Ile | Glu | Asp | Val | Phe | Gln | Asp | Met | Thr | Glu | Gly | Asp | Glu |
|     | 1475 |     |     |     | 1480 |     |     |     | 1485 |     |     |
| Arg | Gln | Trp | Met | Tyr | Ser | Glu | Asn | Ile | Ile | Phe | Cys | Arg | Asp | Thr |
|     | 1490 |     |     |     | 1495 |     |     |     | 1500 |     |     |
| Phe | Phe | Cys | Cys | Asp | His | Ala | Gln | Ser | Cys | Asp | Asp | Asn | Glu | Arg |
|     | 1505 |     |     |     | 1510 |     |     |     | 1515 |     |     |
| Asp | Met | Thr | Trp | Glu | Asp | Glu | Glu | Arg | Arg | Arg | Trp | Lys | Met | Arg |
|     | 1520 |     |     |     | 1525 |     |     |     | 1530 |     |     |
| Lys | Glu | Leu | Phe | Pro | Thr | Ile | Ala | Asp | Asp | Ala | Ile | Ile | Leu | Ala |
|     | 1535 |     |     |     | 1540 |     |     |     | 1545 |     |     |
| Asn | Phe | Asn | Gln | Leu | Tyr | Lys | Ala | Arg | Glu | Thr | Asn | Leu | Arg | Gln |
|     | 1550 |     |     |     | 1555 |     |     |     | 1560 |     |     |
| Thr | Ala | Glu | Ala | Trp | Ala | Gly | Ala | Glu | Val | Ala | Ser | Arg | Leu | Val |
|     | 1565 |     |     |     | 1570 |     |     |     | 1575 |     |     |
| Phe | Thr | Asp | Val | Ala | Pro | Lys | Asn | Gln | His | Ile | Asn | Arg | Ala | Arg |
|     | 1580 |     |     |     | 1585 |     |     |     | 1590 |     |     |
| Val | Cys | Asp | Leu | Phe | Leu | Asp | Thr | Ala | Glu | Cys | Asn | Ala | His | Thr |
|     | 1595 |     |     |     | 1600 |     |     |     | 1605 |     |     |
| Thr | Ala | Ala | Asp | Val | Leu | Trp | Ser | Ser | Thr | Pro | Leu | Leu | Thr | Leu |
|     | 1610 |     |     |     | 1615 |     |     |     | 1620 |     |     |
| Pro | Arg | Tyr | Ser | Tyr | Lys | Met | Cys | Ser | Arg | Met | Ala | Ala | Ser | Ile |
|     | 1625 |     |     |     | 1630 |     |     |     | 1635 |     |     |
| Leu | Arg | Gly | Ala | Leu | Pro | Lys | Ser | Ala | Glu | Gly | Gln | Gln | Ala | Ala |
|     | 1640 |     |     |     | 1645 |     |     |     | 1650 |     |     |
| Leu | Glu | Leu | Ile | Ala | Asp | Gly | Glu | Thr | Glu | Tyr | Glu | Asp | Gln | Ala |
|     | 1655 |     |     |     | 1660 |     |     |     | 1665 |     |     |
| Ala | Glu | Leu | Ala | Gly | Gly | Leu | Thr | Tyr | Val | Met | Thr | Asp | Glu | Gly |
|     | 1670 |     |     |     | 1675 |     |     |     | 1680 |     |     |
| Tyr | Gly | Arg | Gly | Lys | Gly | Arg | Leu | Ala | Glu | Leu | Arg | Lys | Leu | Leu |
|     | 1685 |     |     |     | 1690 |     |     |     | 1695 |     |     |
| Trp | Asp | Ser | Arg | Trp | Ser | Cys | Gly | Leu | Phe | Asn | Thr | Arg | Arg | Trp |
|     | 1700 |     |     |     | 1705 |     |     |     | 1710 |     |     |
| Val | Asn | Asp | Leu | Glu | Arg | Ala | Tyr | Glu | Glu | Ala | Trp | Arg | Arg | Trp |
|     | 1715 |     |     |     | 1720 |     |     |     | 1725 |     |     |
| Val | Ala | Gly | Lys | Gly | Gly | Asp | Ile | Tyr | Leu |     |     |
|     | 1730 |     |     |     | 1735 |     |     |     |     |     |     |

<210> SEQ ID NO 3

```
<211> LENGTH: 859
<212> TYPE: PRT
<213> ORGANISM: Trichoderma reesei

<400> SEQUENCE: 3

Met Pro His Arg Glu Arg Gly Lys Gln Arg Glu Gly Gly Asp Ser Tyr
1               5                   10                  15

Arg Pro Ser Arg Pro Ala Arg Ser Arg Ser Arg Ser Arg Ser Pro Pro
            20                  25                  30

Arg Ala Pro Val Pro Val Arg Thr Glu Glu Lys Gln Ala Ala Ala
        35                  40                  45

Lys Ala Glu Tyr Glu Lys Leu Leu Asn Met Arg Ser Gly Gly Thr Tyr
50                  55                  60

Ile Pro Pro Ala Arg Leu Arg Ala Leu Gln Ala Gln Ile Thr Asp Lys
65                  70                  75                  80

Ser Ser Lys Glu Tyr Gln Arg Met Ala Trp Glu Ala Leu Lys Lys Ser
                85                  90                  95

Ile Asn Gly Leu Ile Asn Lys Val Asn Thr Ala Asn Ile Lys His Ile
            100                 105                 110

Val Pro Glu Leu Phe Gly Glu Asn Leu Val Arg Gly Arg Gly Leu Phe
        115                 120                 125

Cys Arg Ser Ile Met Lys Ala Gln Ala Ala Ser Leu Pro Phe Thr Pro
130                 135                 140

Ile Tyr Ala Ala Met Ala Ala Ile Val Asn Thr Lys Leu Pro Gln Val
145                 150                 155                 160

Gly Glu Leu Leu Val Lys Arg Leu Ile Met Gln Phe Arg Lys Gly Phe
                165                 170                 175

Lys Arg Asn Asp Lys Ala Val Cys Leu Ser Ser Thr Thr Phe Leu Ala
            180                 185                 190

His Leu Ile Asn Gln Gln Val Gln His Glu Met Leu Ala Gly Gln Ile
        195                 200                 205

Leu Leu Leu Leu Leu His Lys Pro Thr Asp Asp Ser Val Glu Ile Ala
210                 215                 220

Val Gly Phe Cys Lys Glu Val Gly Gln Tyr Leu Glu Glu Met Gln Pro
225                 230                 235                 240

Ala Ile Ser Met Ala Val Phe Asp Gln Phe Arg Asn Ile Leu His Glu
                245                 250                 255

Ser Asp Ile Asp Lys Arg Thr Gln Tyr Met Ile Glu Val Leu Phe Gln
            260                 265                 270

Ile Arg Lys Asp Lys Phe Lys Asp His Pro Ala Ile Lys Glu Glu Leu
        275                 280                 285

Asp Leu Val Glu Glu Glu Asp Gln Ile Thr His Lys Val Glu Leu Asp
290                 295                 300

Gly Glu Ile Asp Val Gln Asp Gly Leu Asn Ile Phe Lys Tyr Asp Pro
305                 310                 315                 320

Glu Trp Glu Glu His Glu Ala Tyr Lys Arg Leu Lys Ala Glu Ile
                325                 330                 335

Leu Gly Glu Ala Ser Asp Asp Glu Glu Gly Asp Glu Asp Glu Asp Glu
            340                 345                 350

Asp Glu Ser Ser Glu Asp Glu Asn Glu Glu Thr Lys Ala Met Glu
        355                 360                 365

Ile Lys Asp Gln Ser Asn Ala Asp Leu Val Asn Leu Arg Arg Thr Ile
370                 375                 380

Tyr Leu Thr Ile Met Ser Ser Ala Asp Pro Glu Glu Ala Val His Lys
```

-continued

```
            385                 390                 395                 400
    Leu Met Lys Ile Asn Leu Pro Val Gly Gln Glu Pro Glu Leu Pro Ser
                    405                 410                 415

Met Ile Val Glu Cys Cys Ser Gln Glu Lys Thr Tyr Thr Lys Phe Phe
                    420                 425                 430

Gly Leu Ile Gly Glu Arg Phe Ala Lys Ile Asn Arg Leu Trp Cys Asp
                    435                 440                 445

Leu Phe Glu Gln Ala Phe Val Lys Tyr Glu Thr Ile His Arg Tyr
    450                 455                 460

Glu Asn Asn Lys Leu Arg Asn Ile Ala Met Leu Phe Gly His Met Phe
    465                 470                 475                 480

Ala Ser Asp Ala Leu Gly Trp His Cys Leu Ser Val Ile His Leu Asn
                    485                 490                 495

Glu Glu Glu Thr Thr Ser Ser Ser Arg Ile Phe Ile Lys Ile Leu Phe
                    500                 505                 510

Gln His Ile Ser Glu Glu Ile Gly Leu Ala Lys Leu Arg Ala Arg Met
                    515                 520                 525

Thr Asp Glu Thr Leu Arg Pro Ser Leu Glu Gly Leu Phe Pro Arg Glu
                    530                 535                 540

Asn Pro Arg Asn Ile Arg Phe Ser Ile Asn Tyr Phe Thr Ser Ile Gly
    545                 550                 555                 560

Met Gly Val Leu Thr Glu Glu Met Arg Glu His Leu Met Asn Met Pro
                    565                 570                 575

Lys Pro Ala Leu Pro Ala Pro Ala Ala Gln Asp Arg Ser Asp Thr Asp
                    580                 585                 590

Ser Val Ser Ser Tyr Ser Ser Tyr Thr His Ser Ser Tyr Ser Ser Arg
                    595                 600                 605

Ser Arg Ser Arg Ser Arg Ser Val Gly Arg Arg Ser Gly Gly Arg Gly
                    610                 615                 620

Arg Ser Leu Ser Arg Thr Pro Arg Gly Ala Arg Ser Arg Ser
    625                 630                 635                 640

Tyr Ser Asp Asp Ser Arg Ser Pro Ser Arg Ser Arg Ser Arg Ser Arg
                    645                 650                 655

Ser Asp Ser Val Ser Thr Arg Gly Arg Arg Ala Ser Tyr Ser Ala
                    660                 665                 670

Ser Pro Pro Arg Arg Gly Gly Arg Arg Val Ala Ser Arg Ser Arg Ser
                    675                 680                 685

Tyr Ser Ser Gly Ser Ser Arg Ser Pro Pro Arg Asn Arg Gly Arg
    690                 695                 700

Ala Arg Ser Asn Ser Tyr Ser Ser Tyr Ser Arg Ser Pro Ser Ser Ser
    705                 710                 715                 720

Pro Arg Arg Gly Arg Asp Ala Asp Ser Ala Ser Pro Pro Arg Arg
                    725                 730                 735

Gly Arg Pro Arg Gln Ser Pro Pro Gly Gly Pro Ala Gly Arg Arg Asn
                    740                 745                 750

Ser Ser Ser Val Gly Ser Gly Gly Pro Arg Lys Lys Pro Arg Arg Asp
                    755                 760                 765

Ser Arg Ser Pro Ser Arg Asp Tyr Ser Ser Arg Ser Pro Ser Arg Ser
                    770                 775                 780

Pro Ser Arg Ser Arg Ser Pro Pro Ala Ala Arg Gly Arg Gly
    785                 790                 795                 800

Ser Tyr Thr Pro Ser Arg Ser Arg Ser Pro Pro Arg Arg Val Arg
                    805                 810                 815
```

```
Asp Gly Ser Pro Gly Arg Leu Arg Gly Gly Arg Ser Pro Ser Pro Pro
              820                 825                 830

Leu Pro Val Lys Arg Arg Tyr Asp Ser Glu Ser Val Ser Arg Ser
        835                 840                 845

Pro Pro Pro Leu Lys Arg Gly Arg Arg Asp Asn
        850                 855

<210> SEQ ID NO 4
<211> LENGTH: 2580
<212> TYPE: DNA
<213> ORGANISM: Trichoderma reesei

<400> SEQUENCE: 4
atgccgcacc gcgagcgcgg caagcagcga gaaggcggcg actcgtaccg ccctcgagg      60 ccagcgcgtt cacgctcgcg ctcgcgatcg ccgcctcgcg cgccggtgcc cgtgcggacg     120
gaggaggaga agcaggcggc ggcaaaggcc gagtacgaga agctgctcaa catgcggtcg     180
ggcggcacgt acatcccgcc ggcgaggctg agggcgctgc aggcgcagat cacggacaag     240
agcagcaagg agtaccagcg gatggcgtgg gaggcgctca agaagagcat caacggcctg     300
atcaacaagg tcaacacggc caacatcaag cacattgtgc ccgagctgtt tggcgagaac     360
ctggtgcgcg ccgcggcct cttctgccgc tccatcatga aggcccaggc cgccagtttg      420
cccttcacgc ccatctacgc cgccatggcc gccattgtca caccaagct gccgcaggtc      480 ggcgagctgc tggtcaagcg cctcatcatg cagttccgca agggcttcaa gcgcaacgac     540
aaggccgtct gtctgtcgtc gaccaccttc ctcgcccacc tcatcaacca gcaggtgcag     600
cacgagatgc tggccggcca gatcctgctg ctgctgctgc acaagccgac cgacgacagc     660
gtcgagattg ccgtgggctt ctgcaaggag gttggccagt acctcgagga gatgcagcct     720
gccatttcca tggccgtctt cgaccagttc cgcaacatcc tccacgagtc cgacattgac     780
aagcgaacgc agtacatgat tgaggtgctc ttccagatca ggaaggacaa gttcaaggat     840 caccccggcca tcaaggagga gctggacttg gtggaggagg aggaccagat cacgcacaag     900
gtggagcttg atggcgagat tgatgtgcag gacggactca acatcttcaa gtacgacccg     960
gagtgggagg agcatgagga ggcatacaag aggctcaagg cggagattct gggcgaagcc    1020
agcgatgacg aggagggcga cgaggacgag gacgaggacg agagctccga agatgaagaa    1080
aacgaagaga caaaggccat ggagatcaag gaccagtcta cgccgacttt ggtcaaccta    1140
cggaggacca tctacctcac catcatgtcg agcgccgacc cagaggaagc agttcacaag    1200
ctgatgaaga tcaacctgcc cgtcggccag gaacccgagc tgccctcgat gattgtcgag    1260
tgttgctcgc aggagaagac gtacaccaag ttctttggct tgatcggcga gcgtttcgcc    1320
aagatcaatc ggctgtggtg cgacctcttt gagcaggcct ttgtcaagta ctacgagacg    1380
atccaccgat acgaaaacaa caagctgcgg aacattgcca tgctgtttgg ccacatgttt    1440
gcttccgacg ctctgggctg gcactgcctt tccgtcattc acctcaacga ggaggagacc    1500
acgtcgagca gccgcatctt catcaagatt ctgttccagc acatttccga ggaaatcggc    1560
ctggctaagc tccgggcacg catgactgac gagacgctgc ggcccagcct cgaaggcctc    1620
ttccccagag agaaccctcg caacatccga ttctccatca actacttcac cagcatcggc    1680
atgggtgtac tgaccgagga gatgcgagag cacctcatga acatgccaa gcctgcgctg     1740 cccgcccctg ctgctcagga ccgctcggat acggactccg tctcgagcta ttcgtcttac    1800
actcactcat catactcttc ccgctcgcgc tcacggtccc gatctgtggg tcgtcggagc    1860
```

```
ggcggtcgag gccgatcgct ttcccgaact ccgcctcgac gtggcgcaag gagccgatcc    1920
tactctgacg actcacggtc accgtcgcgg tcaagatcac gatcccgctc cgattccgtc    1980
tctactcgtg ggcgaaggcg agcgtcgtac tcggccagtc ctccccggcg tggtggccgt    2040
cgggttgcca gcagaagccg aagctactcg tcgggctcct cacggtctcc gccaccacgg    2100
aaccgcggtc gcgcacgaag caactcgtat agttcctaca gccgctctcc atcttcttca    2160
ccacgacgcg gcagagacgc agactcggcc agcccgcctc cgcgaagggg tcgaccgcgc    2220
cagagcccac caggcggtcc cgcaggtcga aggaacagct cgtctgtcgg cagcggaggg    2280
ccccgcaaga agcccgacg ggacagccga tcgccgtctc gcgactattc gtcccggtcc    2340
ccgtctcggt cgccgtcgag atctcgatcg cctccgccgg ctgcgcgtgg ccgaaggggc    2400
tcttatacgc cgtcacgcag ccgcagcccc cctccgcgca gggtgaggga tggctcgccg    2460
ggtcgtctga ggggtgggag gtcgcctagt cctcctttgc cggtgaagag gaggcggtat    2520
gatagcgaga gtgtttctcg gtcgccgcct cctttgaagc gcgggagaag ggataactaa    2580
```

<210> SEQ ID NO 5
<211> LENGTH: 543
<212> TYPE: PRT
<213> ORGANISM: Trichoderma reesei

<400> SEQUENCE: 5

```
Met Thr Val Leu Thr Ser Pro Leu Ala Ser Tyr Asn Val Ala Asn Lys
1               5                   10                  15

Leu Tyr Lys Thr Thr Leu Leu Asn Thr Val Cys Leu Val Ala Gly Leu
            20                  25                  30

Ser Ile Phe Phe Phe Gly Tyr Asp Gln Gly Leu Met Gly Gly Val Asn
        35                  40                  45

Thr Thr Arg Asp Tyr Ala Glu Arg Met Gly Phe Gly His Trp Asp Glu
    50                  55                  60

Asp Gln Asn Ile Val Val Asp Lys Pro Leu Gln Gly Gly Ile
65                  70                  75                  80

Val Ala Val Tyr Tyr Leu Pro Gly Thr Leu Cys Gly Cys Leu Leu Gly
                85                  90                  95

Gly Trp Leu Gly Asp Arg Tyr Gly Arg Ile Lys Thr Ile Ala Ile Ala
            100                 105                 110

Cys Ala Trp Ser Val Cys Ala Ala Ala Leu Gln Ala Ser Ala Met Asn
        115                 120                 125

Ala Asn Trp Met Phe Cys Ala Arg Val Leu Asn Gly Val Gly Thr Gly
    130                 135                 140

Ile Leu Asn Ala Ile Thr Pro Val Trp Ala Thr Glu Thr Ala Ala His
145                 150                 155                 160

Thr Ser Arg Gly Gln Phe Val Ser Ile Glu Phe Thr Leu Asn Ile Leu
                165                 170                 175

Gly Val Val Ala Tyr Trp Leu Glu Phe Gly Thr Ser Lys Tyr His
            180                 185                 190

Asp Asn Thr Ser Ser Phe Ile Trp Arg Phe Pro Val Ala Phe Gln Ile
        195                 200                 205

Leu Pro Leu Ile Leu Leu Phe Leu Ile Ile Trp Ile Met Pro Glu Ser
    210                 215                 220

Pro Arg Trp Leu Val Lys Val Gly Arg Glu Glu Ala Arg Phe Ile
225                 230                 235                 240

Leu Gly Arg Leu Arg Gly Asn Glu Gly Glu Asp Gly Leu Lys Ala Glu
```

245                 250                 255
Ala Glu Tyr Asn Asp Ile Val Asn Ile His Lys Leu Glu Val Asp Thr
                260                 265                 270

Ala Lys Gln Gln Ser Tyr Phe Ser Met Phe Phe Gly Ile Gly Ser Gly
            275                 280                 285

Lys Leu His Thr Gly Arg Arg Val Gln Leu Val Ile Trp Leu Gln Ile
        290                 295                 300

Leu Gln Glu Trp Ile Gly Ile Ala Gly Ile Thr Ile Tyr Gly Pro Glu
305                 310                 315                 320

Ile Phe Thr Ile Ala Gly Ile Ser Ala Lys Asp Arg Leu Trp Val Ser
                325                 330                 335

Gly Ile Asn Asn Ile Thr Tyr Met Phe Ala Thr Leu Ile Cys Val Phe
                340                 345                 350

Thr Ile Asp Arg Ile Gly Arg Arg Trp Thr Leu Tyr Trp Gly Ala Val
            355                 360                 365

Gly Gln Gly Ile Cys Met Phe Val Ala Gly Gly Leu Ala Arg Ala Thr
        370                 375                 380

Ile Asn Ala Ser Gly Lys Ala Ser Gln Ser His Ile Gly Gly Ala Ala
385                 390                 395                 400

Thr Phe Phe Val Phe Leu Tyr Thr Ala Ile Phe Gly Ala Thr Trp Leu
                405                 410                 415

Thr Val Pro Trp Leu Tyr Pro Ala Glu Ile Phe Pro Leu Gln Val Arg
            420                 425                 430

Ala Lys Gly Asn Ala Trp Gly Val Val Gly Trp Ser Ile Gly Asn Gly
        435                 440                 445

Trp Cys Val Leu Leu Pro Thr Ile Phe Lys Ala Leu Asn Glu Lys
    450                 455                 460

Thr Leu Tyr Ile Phe Gly Ala Val Asn Ala Leu Ser Ile Leu Val Val
465                 470                 475                 480

Trp Ala Leu Tyr Pro Glu Ser Asn Gln Arg Thr Leu Glu Glu Met Asp
                485                 490                 495

Leu Val Phe Ala Ser Asp Ser Ile Trp Ala Trp Glu Ala Glu Arg Asn
            500                 505                 510

Phe Ala Lys Leu Lys Ala Glu Asn Pro Asp Leu Val Gln Gly Ser Thr
        515                 520                 525

Asn His Gly Val Val Asp Ile Glu Gln Val Ala Glu Pro Lys Glu
    530                 535                 540

<210> SEQ ID NO 6
<211> LENGTH: 1870
<212> TYPE: DNA
<213> ORGANISM: Trichoderma reesei

<400> SEQUENCE: 6
atgaccgtcc tcacctcacc tctggccagc tataatgtgg ccaacaagct gtacaaaacc      60
actctgctca acaccgtctg cctcgtggcc ggactgtcga tcttcttctt cggctatgat     120
cagggattga tgggcggtgt taacacgacg cgcgactatg ccgagcgcat gggctttggc     180
cactgggacg aagaccagaa cattgtcgtc gtcgataagc cgctgctgca gggcggtatc     240
gtagctgtct actatctccc cggaacgctg tgcggttgtc tgcttggcgg ttggcttggt     300
gatcgctatg ccgtatcaa acaattgcc attgcctgtg cgtggagtgt ctgcgcagcc      360
gccctgcagg cctcagctat gaatgcgaac tggatgtttt gcggtatgtc gatgattctt     420
ggacaatcac aaccgaacta ttactgatga tgagatgaaa cagcccgcgt tctgaacggc     480

```
gtcggcactg gaatcttgaa cgcaatcacg cctgtgtggg caaccgagac tgctgctcac    540
acttctcgag gccagttcgt ttccattgag ttcaccctca acattcttgg tgttgttgta    600
gcctactggc tggaattgta cgtgcctcct cactcaggat ccccagtctt gtggaaagtc    660
tccctaatgc ggtggcagtg gtacttctaa atatcacgac aacacatcct ccttcatctg    720
gagattcccg gtcgccttcc agatcctccc cctaatcctt ctgttcctca tcatctggat    780
catgcctgaa tcccccgct ggctcgtcaa agtgggtcgt gaagaagagg ctcgcttcat    840
ccttggtcgt ctccgtggca atgagggcga ggacggcctc aaggcggaag cagagtacaa    900
tgatattgtc aacatccaca agcttgaagt agacaccgcc aagcagcaga gctacttctc    960
catgttcttt ggcattgggt ctggaaagct acacactggc cggcgcgtgc agctggtcat   1020
ctggctccag atattgcaag agtggatcgg tattgcggga atcaccattt acggccctga   1080
gatctttacg attgctggca tcagcgcaaa ggacagactc tgggttagcg ggatcaacaa   1140
tatcacatac atggtacgtt tagccaacac ctcctcacct caaagattcc atcacactaa   1200
cacgggagca gttcgccaca ctgatctgcg tcttcaccat cgatcgcata ggtcgccgtt   1260
ggactctgta ctggggagct gtcggccagg gcatttgcat gttcgtcgcc ggtgcctcg    1320
ctcgcgcaac catcaatgcc tcaggcaaag caagccagag ccacatcggc ggcgctgcaa   1380
cattctttgt gttcctctac actgccattt tcggcgctac ctggctgacg gttccttggt   1440
tgtatccggc cgagattttc cctctgcagg ttagagccaa gggaaatgcc tggggtgtcg   1500
ttggctggtc cattggcaac ggctggtgtg taagtgcact tttcattctc ctctcccgtc   1560
tgggctcttc tggtctaatc ttctctaggt gctcctgctt cctacgatct tcaaggcgct   1620
caacgaaaag acactctaca ttttttggcgc cgtcaacgcc ctgtccatcc tcgtcgtgtg   1680
ggctctgtac cccgaatcga atcaacgaac tctagaggag atggacctcg tctttgctag   1740
cgacagcatc tgggcctggg aggctgagcg taattttgcc aagctcaagg ctgaaaaccc   1800
ggatcttgtt cagggctcaa caaaccacgg agttgtagat attgagcaag ttgccgagcc   1860
aaaggagtag                                                           1870
```

<210> SEQ ID NO 7
<211> LENGTH: 735
<212> TYPE: PRT
<213> ORGANISM: Trichoderma reesei

<400> SEQUENCE: 7

```
Met Ala Val Asn Arg Ile Arg Gly Ala Phe Ala Pro Arg Lys Gly
1               5                   10                  15

Glu Thr Phe Glu Leu Arg Ala Gly Leu Val Ser Gln Tyr Ala Tyr Glu
                20                  25                  30

Arg Lys Glu Ser Ile Gln Lys Thr Ile Met Ala Met Thr Leu Gly Lys
            35                  40                  45

Asp Val Ser Ala Leu Phe Pro Asp Val Leu Lys Asn Ile Ala Thr Ser
        50                  55                  60

Asp Leu Asp Gln Lys Lys Leu Val Tyr Leu Tyr Leu Met Asn Tyr Ala
65                  70                  75                  80

Lys Thr His Pro Asp Leu Cys Ile Leu Ala Val Asn Thr Phe Val Gln
                85                  90                  95

Asp Ser Glu Asp Pro Asn Pro Leu Val Arg Ala Leu Ala Ile Arg Thr
            100                 105                 110

Met Gly Cys Ile Arg Val Asp Lys Met Val Asp Tyr Met Glu Glu Pro
```

```
              115                 120                 125
Leu Arg Lys Thr Leu Arg Asp Glu Ser Pro Tyr Val Arg Lys Thr Ala
            130                 135                 140
Ala Ile Cys Val Ala Lys Leu Phe Asp Leu Asn Pro Ala Met Cys Ile
145                 150                 155                 160
Glu Asn Gly Phe Ile Glu Thr Leu Gln Glu Met Ile Gly Asp Pro Asn
                165                 170                 175
Pro Met Val Val Ala Asn Ser Val Gln Ala Leu Ala Glu Ile Ser Glu
                180                 185                 190
Thr Ala Pro Glu Thr Arg Ala Leu Leu Val Thr Pro Val Leu Lys
                195                 200                 205
Lys Leu Leu Met Ala Met Asn Glu Cys Thr Glu Trp Gly Arg Ile Thr
            210                 215                 220
Ile Leu Thr Val Leu Ala Asp Tyr Ala Ala Thr Asp Val Lys Glu Ser
225                 230                 235                 240
Glu His Ile Cys Glu Arg Val Ile Pro Gln Phe Gln His Val Asn Pro
                245                 250                 255
Ser Val Val Leu Ala Ala Val Lys Val Phe Ile His Met Lys Ser
                260                 265                 270
Ile Asn Pro Glu Leu Val Arg Ser Tyr Leu Lys Lys Met Ala Pro Pro
                275                 280                 285
Leu Val Thr Leu Val Ala Ser Ala Pro Glu Val Gln Tyr Val Ala Leu
            290                 295                 300
Arg Asn Ile Asp Leu Leu Leu Gln Ala Lys Pro Asp Ile Leu Ser Lys
305                 310                 315                 320
Glu Leu Arg Val Phe Phe Cys Lys Tyr Asn Asp Pro Tyr Val Lys
                325                 330                 335
Met Gln Lys Leu Glu Ile Met Val Arg Ile Ala Asn Glu Lys Asn Tyr
            340                 345                 350
Glu Gln Leu Leu Ser Glu Leu Lys Glu Tyr Ala Leu Glu Val Asp Met
            355                 360                 365
Asp Phe Val Arg Arg Ala Ile Lys Ala Ile Gly Gln Val Ala Ile Lys
            370                 375                 380
Ile Glu Glu Ala Ser Gly Lys Cys Val Gln Ala Leu Glu Asp Leu Leu
385                 390                 395                 400
Ala Thr Lys Val Asn Tyr Val Gln Glu Val Val Val Ile Lys
                405                 410                 415
Asp Ile Leu Arg Lys Tyr Pro Gly Tyr Glu Gly Val Ile Pro Ser Leu
                420                 425                 430
Cys Asn Tyr Ile Asp Glu Leu Asp Glu Ala Asn Ala Arg Gly Ser Leu
            435                 440                 445
Ile Trp Ile Val Gly Glu Tyr Ala Glu Lys Ile Ser Asn Ala Glu Glu
            450                 455                 460
Ile Leu Glu Gly Phe Val Asp Thr Phe Leu Glu Glu Phe Thr Gln Thr
465                 470                 475                 480
Gln Leu Gln Ile Leu Thr Ala Val Val Lys Leu Phe Leu Lys Lys Pro
                485                 490                 495
Ser Gly Ala Gln Gly Leu Val Gln Lys Val Leu Gln Glu Ala Thr Thr
                500                 505                 510
Asn Asn Asp Asn Pro Asp Ile Arg Asp Arg Ala Tyr Val Tyr Trp Arg
            515                 520                 525
Leu Leu Ser Gly Asp Leu Glu Val Ala Lys Asn Ile Val Leu Ser Gln
            530                 535                 540
```

Lys Pro Thr Ile Ser Thr Thr Met Thr Ser Leu Pro Thr Ala Leu Leu
545                 550                 555                 560

Glu Gln Leu Leu Ser Glu Leu Ser Thr Leu Ala Ser Val Tyr His Lys
            565                 570                 575

Pro Pro Glu Ala Phe Val Gly Lys Gly Arg Phe Gly Ala Asp Glu Ile
        580                 585                 590

Gln Arg Ala Ala Ile Gln Glu Gln Arg Gln Asn Ala Ala Glu Asn Pro
    595                 600                 605

Ile Ala Ala Ser Val Ala Ala Ala Ala Asn Gly Ser Ser Ser Val
610                 615                 620

Ser Gln Asn Asn Ile Glu Asn Leu Leu Asp Ile Asp Phe Asp Gly Ala
625                 630                 635                 640

Ala Pro Ala Ser Gln Glu Gln Asn Ser Ala Ala Gly Thr Pro Asp Arg
            645                 650                 655

Val Ser Ser Pro Ala Thr Gly Gly Met Ala Asp Met Met Ser Met Phe
        660                 665                 670

Asp Ala Pro Pro Ala Gly Ser Ser Gly Ala Pro Ser Gly Gly Met
    675                 680                 685

Asn Asp Leu Met Asn Gly Phe Glu Gly Leu Asn Phe Gly Ala Thr Ser
690                 695                 700

Thr Asn Gln Pro Leu Pro Ala Ala Met Gln Leu His Asn Ala Gln Gly
705                 710                 715                 720

Gly Ser Gln Pro Lys Lys Asp Ser Asp Asp Leu Leu Gly Leu Leu
            725                 730                 735

<210> SEQ ID NO 8
<211> LENGTH: 2589
<212> TYPE: DNA
<213> ORGANISM: Trichoderma reesei

<400> SEQUENCE: 8

```
atggcggtga atcgcatccg gggcgccttt gccgcgcctc ggaagggaga gacattcgag      60
ctgcgggccg gcctggtgtc gcagtatgcc tacgagcgga aggagtccat ccagaagacc     120
atcatggcca tgacgctggg caaggacgtg tccgccctgt tcccagacgt cttgaagaac     180
attgccacgt ccgacctgga ccagaagaag ctggtctacc tctacctcat gtatgtggct     240
gcagacaatg gccgaccatg atcacacaca cggagcgaag gacgagatac tgcctgacgt     300
ggcgatgcgg tgctaacgtg gagtgtgacc ccaggaacta cgcaaagaca cacccagacc     360
tctgcattct cgccgtcaac acgttcgtgc aagactcgga gacccgaac ccgctggtgc      420
gagcgctggc catccgcaca atgggctgca tccgggtgga caagatggtc gactacatgg     480
aggagccgct gcggaagacg ctgcgggacg agtcgccgta cgtgcgcaag acggccgcca     540
tctgcgtggc caagctgttc gacctgaacc cggccatgtg catcgagaac ggcttcatcg     600
agacgctgca ggagatgatt ggcgacccga accccatggt ggtcgcaaac tcggtccagg     660
cgctggccga gattagcgag acggcgcccg agacgcgggc gctgctggtg acgccccgg      720
tgctcaagaa gctgcttatg ccatgaacg aatgcaccga atggggtaga atcaccattc      780
tgaccgtgct ggcagactac gctgccaccg acgtcaagga gtcggagcac atctgcgaga     840
gggtcattcc gcagttccag cacgtcaacc ctagcgtggt cctggctgct gtcaaggtgg     900
tctttattca tatgaagtcg attaacccgg agctcgtgcg gtcatatctt aagaagatgg     960
cgcctccact cggtgcgttc cgatcatgtc cccgatttga catctgagaa gacatgacgt    1020
```

-continued

```
gactatgcta acactgcagc ttgtatacag tcacactggt tgcttctgcc cccgaggtcc    1080
aatacgtcgc tctcagaaac attgatctgc tccttcaagc caagcccgac atcctgagca    1140
aagagttaag agtcttcttt tgcaaataca acgacccgcc gtacgtcaag atgcaaaagc    1200
tggaaatcat ggtcaggata gcaaacgaaa agaactacga gcagctcctg tctgagctca    1260
aggaatacgc cctggaagtg gacatggact ttgtgcgccg agccatcaag gccatcggcc    1320
aggtggccat caagattgag gaggccagtg gcaagtgcgt gcaggcgctg aagatcttc     1380 tcgctaccaa ggtcaactac gtggtgcaag aggttgtcgt ggtcatcaaa gatatcctgc    1440
gaaagtaccc cggttacgag ggcgtgatcc cctcgctctg caactacatt gacgagctcg    1500
acgaggccaa tgctcgtgga tccctcatct ggattgtggg agagtacgcc gagaagatta    1560
gcaacgctga ggagattctg gagggttttg tagacacctt tttggaggag ttcactcagg    1620
tatgtggaga gctgtggaaa agtcggggat tttggctaat cgaactgcag acacaactcc    1680
agatccttac agctgttgtt aagctgtttt tgaagaagcc gagtggcgcg cagggcctgg    1740
ttcagaaggt gctgcaggag caacaacca acaacgacaa ccccgatatc cgcgacagag    1800
catacgtcta ctggcgattg ttatcgggag atttggaggt ggccaaggta ggagtcgttg    1860
gcgtcctttg atgagagctg cgcatactga cggatctcaa gaacattgtc ctgtcacaga    1920
agccgaccat ttcaacaaca atgacaagcc tgccgactgc gctactggag cagctgctgt    1980
cggagctgtc aactctggcg tcggtatacc acaagccccc ggaagccttt gtcggcaagg    2040
gccggttcgg tgccgacgag atccagcgag ccgccatcca ggagcagcgc cagaacgccg    2100
cggaaaaccc catcgccgca tccgtggctg ccgccgccgc caatggctcc tcgtcggtct    2160
cgcaaaacaa cattgagaac ctgctggaca ttgactttga cggcgcagca ccggcctctc    2220
aggagcagaa cagcgcggcg ggaacacctg accgggtgtc gagcccggcc acgggtggca    2280
tggccgacat gatgagcatg tttgatgcgc ctccggctgg cagctctgga ggtgctccgt    2340
ccggcggcat gaacgacttg atgaacggat ttgaggggct caactttggg gccacgagta    2400
caaatcagcc gttgccggcg gcgatgcagc tgcacaatgc gcaaggcggc tctcagccga    2460
agaaggatag cgatgatctt ttgggttttgt tgtaaatgtt ggaggagcgt atatgcatgc    2520
aagcagcaag ccagaagggg agaagaatcg acaagagaga ctggaggagg aggcaaggga    2580
gggggggg                                                             2589
```

<210> SEQ ID NO 9
<211> LENGTH: 5723
<212> TYPE: DNA
<213> ORGANISM: Artificial Sequence
<220> FEATURE:
<223> OTHER INFORMATION: DNA fragment for transformation

<400> SEQUENCE: 9

```
cttaagacag cctaggaaag tgatgtgcac aggggtaaca tagttcaaga ttgaaagtaa      60
acatacctag tacctaggta atatttagtg atgtgcatgt gcaagatgtt gatatagaga     120
aacttttcat ttcagttctg tccatcacgt cttccaggct catcttgtgg catctggaga     180
caagaaaaag gcagccgtct gcaagacatg aaacggtaca tcagcatcaa ctccgaatcc     240
cccatgctca catccaacaa attccgacaa accccacgtt gggtgagtat aagctgcgag     300
gccatgcacc ccgtttctga gctattgctg ccgcgtctcc gctagtgctc ccagagagat     360
taggagacag tgttggtggc ctgtgatagg gcgtcgatga ggaaatttc acttctctgc     420 cattctatct cgcaatatgt tactgtaata gcaaccaaca tgctccggcg acgctaaggc     480
```

```
aatgcttcct tacttcatga cgtcttcatg cttattttga atttggcctg tcatattcat    540
atgagttaca taccgcactg cagtggcaca acctacctta ctactactag tagtactaaa    600
cttacagtac gactagcact gcgatcccca tccaattcta gtggcatcca tctaccggca    660
ctacctacct actaaggtat tacatactcg cccaaggcag tgggagcgca ctccaatcaa    720
tcctctcatt cattccttac taacaccttt tgacgctcac atgtaaatat gctttctccc    780
ctgcgctcgc ggcttgtgaa agccacattc ctgggcacat gtcgccaagt gcgattggcc    840
tcttcagcga gatatcccca ggccgtctcg cctctagcct ttgacctcca ttcgccttcc    900
cacccgagta aagatgagaa gacggctccc atcatcttcc tgcatggtct ctttgggtcc    960
aagaagaaca acagggcaat cagcaagtaa gcgatgattc atcgtgtgct gtcatggtct   1020
ctagcttaca atatcgtaga gccctggccc gagacttgaa gactcatgta tacacggtgg   1080
taggtgaagt ctgcgaggct gttcaagcaa gtttcatcag cgactaaaca ggaatgaagg   1140
atctgagaaa ccacggagaa tctccccacg atccccgcca cgactatgtc gccatgaccg   1200
aggacctgtt ggccttcatt gaccagcatg gtctcaaaga acctactctg ataggccatt   1260
ccatgtgcgg ccgcctagtc atcattggat aggcagatta ctcagcctga atgacatcaa   1320
catgttaccc atgatacaat aggtcacaca aacaagcgct aagatgcact tggtatgaca   1380
agcccagtag tccgtttcaa aagacctaga tgatgaacta caacatgagg tgttgcctcc   1440
tgatccagtc caactgcaaa cgctgatgta tactcaatca agcctgatgt aaatgctgcg   1500
actcgattcg ctggatatga agatcaaaga gagctctgat gggtccaata tagccgggtt   1560
ttgttaggac agtccaccac accgatatta gaattggtca agcaccttat catttcatag   1620
agattgcggt ttctagatct acgccaggac cgagcaagcc cagatgagaa ccgacgcaga   1680
tttccttggc acctgttgct tcagctgaat cctggcaata cgagatacct gctttgaata   1740
ttttgaatag ctcgcccgct ggagagcatc ctgaatgcaa gtaacaaccg tagaggctga   1800
cacggcaggt gttgctaggg agcgtcgtgt tctacaaggc cagacgtctt cgcggttgat   1860
atatatgtat gtttgactgc aggctgctca gcgacgacag tcaagttcgc cctcgctgct   1920
tgtgcaataa tcgcagtggg gaagccacac cgtgactccc atctttcagt aaagctctgt   1980
tggtgtttat cagcaataca cgtaatttaa actcgttagc atggggctga tagcttaatt   2040
accgtttacc agtgccgcgg ttctgcagct ttccttggcc cgtaaaattc ggcgaagcca   2100
gccaatcacc agctaggcac cagctaaacc ctataattag tctcttatca acaccatccg   2160
ctcccccggg atcaatgagg agaatgaggg ggatgcgggg ctaaagaagc ctacataacc   2220
ctcatgccaa ctcccagttt acactcgtcg agccaacatc ctgactataa gctaacacag   2280
aatgcctcaa tcctgggaag aactggccgc tgataagcgc gcccgcctcg caaaaaccat   2340
ccctgatgaa tggaaagtcc agacgctgcc tgcggaagac agcgttattg atttcccaaa   2400
gaaatcgggc atcctttcag aggccgaact gaagatcaca gaggcctccg ctgcagatct   2460
tgtgtccaag ctggcggccg gagagttgac ctcggtggaa gttacgctag cattctgtaa   2520
acgggcagca atcgcccagc agttagtagg gtcccctcta cctctcaggg agatgtaaca   2580
acgccacctt atgggactat caagctgacg ctggcttctg tgcagacaaa ctgcgcccac   2640
gagttcttcc ctgacgccgc tctcgcgcag gcaagggaac tcgatgaata ctacgcaaag   2700
cacaagagac ccgttggtcc actccatggc ctccccatct ctctcaaaga ccagcttcga   2760
gtcaaggtac accgttgccc ctaagtcgtt agatgtccct ttttgtcagc taacatatgc   2820
```

```
caccagggct acgaaacatc aatgggctac atctcatggc taaacaagta cgacgaaggg    2880
gactcggttc tgacaaccat gctccgcaaa gccggtgccg tcttctacgt caagacctct    2940
gtcccgcaga ccctgatggt ctgcgagaca gtcaacaaca tcatcgggcg caccgtcaac    3000
ccacgcaaca agaactggtc gtgcggcggc agttctggtg gtgagggtgc gatcgttggg    3060
attcgtggtg gcgtcatcgg tgtaggaacg gatatcggtg gctcgattcg agtgccggcc    3120
gcgttcaact tcctgtacgg tctaaggccg agtcatgggc ggctgccgta tgcaaagatg    3180
gcgaacagca tggagggtca ggagacggtg cacagcgttg tcgggccgat tacgcactct    3240
gttgagggtg agtccttcgc ctcttccttc ttttcctgct ctataccagg cctccactgt    3300
cctcctttct tgcttttat actatatacg agaccggcag tcactgatga agtatgttag    3360
acctccgcct cttcaccaaa tccgtcctcg gtcaggagcc atggaaatac gactccaagg    3420
tcatccccat gccctggcgc cagtccgagt cggacattat tgcctccaag atcaagaacg    3480
gcgggctcaa tatcggctac tacaacttcg acggcaatgt ccttccacac cctcctatcc    3540
tgcgcggcgt ggaaaccacc gtcgccgcac tcgccaaagc cggtcacacc gtgacccgt    3600 ggacgccata caagcacgat ttcggccacg atctcatctc ccatatctac gcggctgacg    3660
gcagcgccga cgtaatgcgc gatatcagtg catccggcga gccggcgatt ccaaatatca    3720
aagacctact gaacccgaac atcaaagctg ttaacatgaa cgagctctgg gacacgcatc    3780
tccagaagtg gaattaccag atggagtacc ttgagaaatg gcgggaggct gaagaaaagg    3840
ccgggaagga actggacgcc atcatcgcgc cgattacgcc taccgctgcg gtacggcatg    3900
accagttccg gtactatggg tatgcctctg tgatcaacct gctggatttc acgagcgtgg    3960
ttgttccggt taccttttgcg gataagaaca tcgataagaa gaatgagagt ttcaaggcgg    4020
ttagtgagct tgatgccctc gtgcaggaag agtatgatcc ggaggcgtac catggggcac    4080
cggttgcagt gcaggttatc ggacggagac tcagtgaaga gaggacgttg gcgattgcag    4140
aggaagtggg gaagttgctg ggaaatgtgg tgactccata gctaataagt gtcagatagc    4200
aatttgcaca agaaatcaat accagcaact gtaaataagc gctgaagtga ccatgccatg    4260
ctacgaaaga gcagaaaaaa acctgccgta gaaccgaaga gatatgacac gcttccatct    4320
ctcaaaggaa gaatcccttc agggttgcgt ttccagtcta gacgcgttaa ttgaacagat    4380
tgtccgcgat gagattcaca tactagttaa tctcaatggc tacaccagag gtgctcggaa    4440
cgaaatattc gctgctcgcc cggcccctat ccagatgtcc tttatgggat cgccgggac     4500 gcttggtgcg gagtggtgcg actacctcct cgccgacaca acggccgtcc ccccgagcac    4560
tttgcgccct tggaggaaca acaccaccat agaagacgtg tttcaggaca tgaccgaggg    4620
ggatgagcgc cagtggatgt actcggagaa catcatattc tgccgagaca cgttcttctg    4680
ctgtgatcac gcgcagtcgt gcgatgataa tgaacgcgac atgacgtggg aggatgaaga    4740
gaggcgtcgc tggaagatgc gcaaggaact atttccgaca atcgcagacg atgccatcat    4800
cctggccaac tttaatcaac tctacaaggc aagtaaagct tgcatgaaat ggccagcttg    4860
tagtactctt cccagctaac ctgatggtag attgacccga ctacattccg atcttggtta    4920
cgaatcctcg ccaggactcc caaggccata ctctggcttc tacggttccc tgaactagga    4980
gagaccaatt tgcgacaaac ggccgaggcc tgggccgggg cagaggtggc cagtcggctc    5040
gtcttcactg acgttgcgcc aaagaaccag cacatcaaca gggctagagt atgcgatctg    5100
ttcctcgata ctgcggagtg caacgcgcac accactgccg ccgatgtcct gtggtcgagc    5160
actcctctcc tcaccttgcc tcggtattcg tacaagatgt gctcccggat ggcggcgtcc    5220
```

```
atcctgcgag gcgcgctgcc caagtcggca gagggtcaac aggcagcact ggaactgatc      5280
gcggatggcg agacggaata cgaggatcaa gccgcagaac tagccggggg gctcacttac      5340
gtgatgacgg atgagggata cggtcggggc aagggcgtc tagcagagct acgaaaactg       5400
ctttgggata gcagatggag ctgcggactc ttcaacacac ggcggtgggt aaacgatctg      5460
gaaagggctt acgaggaggc atggcgacgg tgggttgcgg gcaagggcgg tgacatatat      5520
ctgtgaaatt ggttgcaaaa tctagatggc gcactttcgt tgtggtaatg ggatgggata      5580
tcacggccat cccggtggtt tgggttcagg gcttttttgc atggatattg ggcgttgcat      5640
ctctggagga acgcaagtac cctccggatg ccaatgggat tttattttgt aagtatccat      5700
ctagctggct agtgggtgca tgc                                              5723
```

<210> SEQ ID NO 10
<211> LENGTH: 37
<212> TYPE: DNA
<213> ORGANISM: Artificial Sequence
<220> FEATURE:
<223> OTHER INFORMATION: Oligo DNA for PCR

<400> SEQUENCE: 10

```
atgcatctta agacagccta ggaaagtgat gtgcaca                               37
```

<210> SEQ ID NO 11
<211> LENGTH: 35
<212> TYPE: DNA
<213> ORGANISM: Artificial Sequence
<220> FEATURE:
<223> OTHER INFORMATION: Oligo DNA for PCR

<400> SEQUENCE: 11

```
atgcggccgc acatggaatg gcctatcaga gtagg                                 35
```

<210> SEQ ID NO 12
<211> LENGTH: 33
<212> TYPE: DNA
<213> ORGANISM: Artificial Sequence
<220> FEATURE:
<223> OTHER INFORMATION: Oligo DNA for PCR

<400> SEQUENCE: 12

```
atacgcgtta attgaacaga ttgtccgcga tga                                   33
```

<210> SEQ ID NO 13
<211> LENGTH: 33
<212> TYPE: DNA
<213> ORGANISM: Artificial Sequence
<220> FEATURE:
<223> OTHER INFORMATION: Oligo DNA for PCR

<400> SEQUENCE: 13

```
atgcatgcac ccactagcca gctagatgga tac                                   33
```